US009987302B2

(12) United States Patent
Otterbein

(10) Patent No.: US 9,987,302 B2
(45) Date of Patent: Jun. 5, 2018

(54) METHODS OF TREATING DNA DAMAGE

(75) Inventor: Leo E. Otterbein, Beverly, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days. days.

(21) Appl. No.: 14/236,756

(22) PCT Filed: Aug. 8, 2012

(86) PCT No.: PCT/US2012/049961
§ 371 (c)(1),
(2), (4) Date: Apr. 2, 2014

(87) PCT Pub. No.: WO2013/022946
PCT Pub. Date: Feb. 14, 2013

(65) Prior Publication Data
US 2014/0243581 A1    Aug. 28, 2014

Related U.S. Application Data

(60) Provisional application No. 61/521,566, filed on Aug. 9, 2011.

(51) Int. Cl.
*A61K 33/00* (2006.01)
*A61N 5/10* (2006.01)
(52) U.S. Cl.
CPC ................. *A61K 33/00* (2013.01); *A61N 5/10* (2013.01); *A61N 2005/1094* (2013.01); *F04C 2270/0421* (2013.01)
(58) Field of Classification Search
CPC .......................... A61N 5/10; A61N 2005/1094
See application file for complete search history.

(56) References Cited

U.S. PATENT DOCUMENTS

| | | |
|---|---|---|
| 6,593,353 B1 | 7/2003 | Gudkov et al. |
| 7,238,469 B2 | 7/2007 | Bach et al. |
| 7,364,757 B2 | 4/2008 | Otterbein et al. |
| 7,678,390 B2 | 3/2010 | Choi et al. |
| 7,687,079 B2 | 3/2010 | Otterbein et al. |
| 7,981,448 B2 | 7/2011 | Otterbein et al. |
| 2003/0064114 A1 | 4/2003 | Motterlini |
| 2003/0068387 A1 | 4/2003 | Roland et al. |
| 2004/0052866 A1 | 3/2004 | Otterbein et al. |

(Continued)

FOREIGN PATENT DOCUMENTS

| | | |
|---|---|---|
| EP | 2741821 A | 6/2014 |
| JP | 2005-525848 | 9/2005 |

(Continued)

OTHER PUBLICATIONS

Supplementary European Search Report issued in EP12821844.3 on Apr. 28, 2015 (7 pages).

(Continued)

*Primary Examiner* — Charles A Marmor, II
*Assistant Examiner* — Carrie R Dorna
(74) *Attorney, Agent, or Firm* — Fish & Richardson P.C.

(57) ABSTRACT

The present invention relates to methods and compositions of treating patients suffering from, or at risk for, DNA damage and to increase life span, i.e., prevent or slow the aging process in all species. The treatment includes administering to the patient a pharmaceutical composition that includes carbon monoxide.

45 Claims, 19 Drawing Sheets

(56) References Cited

U.S. PATENT DOCUMENTS

| | | | |
|---|---|---|---|
| 2004/0131703 A1 | 8/2004 | Bach et al. | |
| 2004/0228930 A1 | 11/2004 | Billiar et al. | |
| 2004/0258772 A1 | 12/2004 | Otterbein et al. | |
| 2005/0080468 A1* | 4/2005 | Christman | A61N 7/00 607/96 |
| 2007/0207217 A1 | 9/2007 | Haas et al. | |
| 2007/0293458 A1 | 12/2007 | Shamsuddin et al. | |

FOREIGN PATENT DOCUMENTS

| | | |
|---|---|---|
| JP | 2005-530737 | 10/2005 |
| JP | 2005-532351 | 10/2005 |
| JP | 2005-533021 | 11/2005 |
| WO | WO 2003/072024 | 9/2003 |
| WO | WO 2003/088981 | 10/2003 |
| WO | WO 2003/096977 | 11/2003 |
| WO | 2003/103585 | 12/2003 |
| WO | WO 2013/022946 | 2/2013 |

OTHER PUBLICATIONS

Weaiel et al., "863 Heme Oxygenase-1 and Carbon Monoxide Modulate Responses to DNA Damage and Arrest Tumour Growth," European Urology Supplements, 9(2):273-274 (2010).

International Search Report and Written Opinion issued in PCT/US12/49961 on Jan. 22, 2013 (11 pages).

Han et al., "Mechanism of protection of bystander cells by exogenous carbon monoxide: Impaired response to damage signal of radiation-induced bystander effect," Mutation Research 709-710:1-6 (2011).

Supplementary European Search Report issued in EP12821844 on Sep. 7, 2015 (5 pages).

International Preliminary Report on Patentability issued in PCT/US12/49961 on Feb. 11, 2014, 8 pages.

Shuryak et al., "A New View of Radiation-Induced Cancer," Radiation Protection Dosimetry, Nov. 27, 2010, ncq389, 7 pages.

Becker-Hapak et al., "TAT-mediated protein transduction into mammalian cells." Methods, Jul. 31, 2001, 24(3):247-56.

Choi et al., "Heme oxygenase-1: function, regulation, and implication of a novel stress-inducible protein in oxidant-induced lung injury." American journal of respiratory cell and molecular biology. Jul. 1996, 15(1):9-19.

Christodoulides et al., "Vascular Smooth Muscle Cell Heme Oxygenases Generate Guanylyl Cyclase-Stimulatory Carbon Monoxide," Circulation May 1, 1995, 97:2306-9.

Garinis et al., "DNA damage and ageing: new-age ideas for an age-old problem," Nat Cell Biol, Nov. 2008, 10(11):1241-1247.

Golob et al., "Acute in vivo testing of an intravascular respiratory support catheter." ASAIO J, Sep.-Oct. 2001, 47(5):432-7.

Hattler et al., "Development of an intravenous membrane oxygenator: enhanced intravenous gas exchange through convective mixing of blood around hollow fiber membranes." Artificial organs. Nov. 1, 1994. 18(11):806-12.

Ingi et al., "Carbon monoxide: an endogenous modulator of the nitric oxide-cyclic GMP signaling system." Neuron. Apr. 1996, 16(4):835-42.

Keyse et al., "Heme oxygenase is the major 32-kDa stress protein induced in human skin fibroblasts by UVA radiation, hydrogen peroxide, and sodium arsenite." Proc Natl Acad Sci USA. Jan. 1989, 86(1):99-103.

Lombard et al., "DNA repair, genome stability, and aging." Cell. Feb. 25, 2005,120(4):497-512.

Maines, "The heme oxygenase system: a regulator of second messenger gases." Annual review of pharmacology and toxicology. Apr. 1997, 37(1):517-54.

Mansouri et al., "Alteration of Platelet Aggregation by Cigarette Smoke and Carbon Monoxide," Thromb Haemost. Dec. 27, 1982, 48(3):286-8.

Morimoto et al., "Real-time measurements of endogenous CO production from vascular cells using an ultrasensitive laser sensor," Am. J. Physiol. Heart. Circ. Physiol, vol. 280, Jan. 1, 2001, pp. H482-H488.

Pozzoli et al., "Carbon Monoxide as a Novel Neuroendocrine Modulator: Inhibition of Stimulated Corticotropin-Releasing Hormone Release from Acute Rat Hypothalamic Explants," Endocrinology Dec. 1, 1994, 135(6):2314-2317.

Sunderman et al., "Gas-chromatographic assay for heme oxygenase activity." Clin. Chem., Oct. 1982, 28(10):2026-2032.

Tenhunen et al., "The enzymatic catabolism of hemoglobin: stimulation of microsomal heme oxygenase by hemin," J. Lab. Clin. Med., Mar. 1970, 75(3)410-421.

Utz et al., "Carbon Monoxide Relaxes Ileal Smooth Muscle Through Activation of Guanylate Cyclase," Biochem Pharmacol. Apr. 15, 1991, 41(8):195-201.

Verma et al, "Carbon monoxide: a putative neural messenger." Science Jan. 15, 1993, 259(5093):381-384.

* cited by examiner

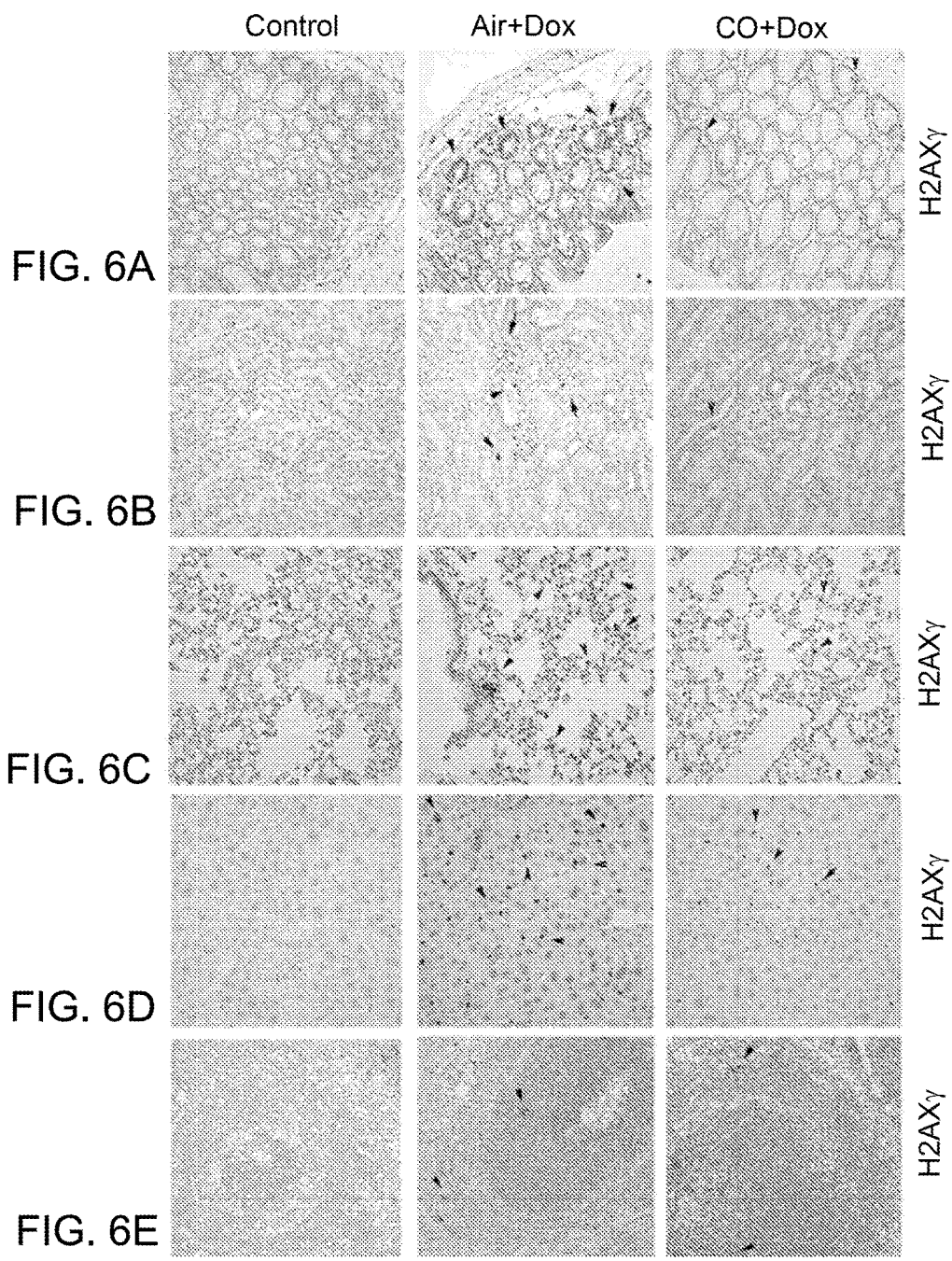

METHODS OF TREATING DNA DAMAGE

CLAIM OF PRIORITY

This application is a U.S. National Phase Application under 35 U.S.C. § 371 of International Patent Application No. PCT/US2012/049961, filed on Aug. 8, 2012, which claims the benefit of U.S. Provisional Patent Application Ser. No. 61/521,566, filed on Aug. 9, 2011, the entire contents of which are hereby incorporated by reference in their entireties.

STATEMENT AS TO FEDERALLY SPONSORED RESEARCH

This invention was made with government support under Grant No. GM088666 awarded by the National Institutes of Health. The Government has certain rights in the invention.

TECHNICAL FIELD

This invention relates to the treatment of DNA damage and/or facilitation of DNA repair.

BACKGROUND

Heme oxygenase-1 (HO-1) catalyzes the first step in the degradation of heme. HO-1 cleaves the α-meso carbon bridge of b-type heme molecules by oxidation to yield equimolar quantities of biliverdin IXa, carbon monoxide (CO), and free iron. Subsequently, biliverdin is converted to bilirubin via biliverdin reductase, and the free iron is sequestered into ferritin (the production of which is induced by the free iron).

CO is recognized as an important signaling molecule (Verma et al., Science 259:381-384, 1993). It has been suggested that carbon monoxide acts as a neuronal messenger molecule in the brain (Verma et al.) and as a neuroendocrine modulator in the hypothalamus (Pozzoli et al., Endocrinology 735:2314-2317, 1994). Like nitric oxide, CO is a smooth muscle relaxant (Utz et al., Biochem Pharmacol. 47:195-201, 1991; Christodoulides et al., Circulation 97:2306-9, 1995) and inhibits platelet aggregation (Mansouri et al., Thromb Haemost. 48:286-8, 1982). Inhalation of low levels of CO has been shown to have anti-inflammatory effects in some models.

Efficient DNA damage repair and checkpoint mechanisms are critical components of normal cellular function to maintain the integrity of genomic DNA (Garinis et al., Nat Cell Biol 10 (11), 1241 (2008); Lombard et al., Cell 120 (4), 497 (2005)). DNA lesions are induced in response to UV or ionizing radiation as well as many chemicals including endogenous metabolites and reactive oxygen species (ROS). DNA repair pathways include repair of damaged bases or single-strand DNA breaks (base excision repair) and repair of double strand DNA breaks (DSB) including homologous recombination (HR) or non-homologous end joining (NHEJ).

SUMMARY

The present invention is based, in part, on the discovery that administration of CO can protect against the development of DNA damage in cells (and/or enhance DNA repair) that may result from exposure to DNA-damaging levels of radiation. Methods described herein are useful, e.g., for treating subjects who have been exposed, are suspected to have been exposed, or will be exposed, to radiation, e.g., from a nuclear reactor or a nuclear weapon, from a radiation therapy (e.g., external beam radiation therapy (e.g., x-rays and/or gamma rays) or radioactive pharmaceutical compound), and/or from radioactive materials.

Accordingly, the present disclosure features methods of administering a genotoxic treatment, e.g., administration of a genotoxic chemotherapeutic agent, radiotherapy, and hyperthermia therapy, to a patient. The method includes administering the genotoxic treatment to the patient, and before, during, and/or after administering the genotoxic treatment, administering to the patient a pharmaceutical composition comprising carbon monoxide in an amount effective to protect cells of the patient and/or reduce DNA damage in the patient.

In one aspect, methods of reducing radiation-induced DNA damage in a subject are provided. The methods include identifying a subject who will be, is being, or has been exposed to DNA-damaging levels of radiation; and administering to the subject a pharmaceutical composition comprising an amount of carbon monoxide effective to reduce radiation-induced DNA damage in the subject.

In one embodiment, the subject will be, is being, or has been exposed to DNA-damaging levels of radiation in their occupation, where the occupation is selected from the group consisting of a health care worker, miner, nuclear energy worker, and airline crew member. In one embodiment, the subject will be, is being, or has been exposed to DNA-damaging levels of radiation from a nuclear reactor or nuclear weapon.

In one embodiment, the pharmaceutical composition is administered before, while, and/or after the subject has been exposed to DNA-damaging levels of radiation.

In one embodiment, the pharmaceutical composition is in gaseous form and is administered to the patient by inhalation. In one embodiment, the pharmaceutical composition is in liquid form and is administered to the patient orally. In one embodiment, the pharmaceutical composition is administered directly to the abdominal cavity of the patient. In one embodiment, the pharmaceutical composition comprises a carbon monoxide-releasing compound. In one embodiment, the pharmaceutical composition is administered by an artificial lung. In one embodiment, the pharmaceutical composition is administered by an extracorporeal membrane gas exchange device.

In another aspect, methods of administering a genotoxic treatment to a patient are featured. The methods include (a) administering the genotoxic treatment to the patient; and (b) before, during, or after step (a), administering to the patient a pharmaceutical composition comprising carbon monoxide in an amount effective to protect cells of the patient, wherein the genotoxic treatment is radiotherapy or hyperthermia therapy.

In one embodiment, the pharmaceutical composition is administered before, during, and/or after step (a). In one embodiment, the pharmaceutical composition is in gaseous form and is administered to the patient by inhalation. In one embodiment, the pharmaceutical composition is in liquid form and is administered to the patient orally. In one embodiment, the pharmaceutical composition is administered directly to the abdominal cavity of the patient. In one embodiment, the pharmaceutical composition comprises a carbon monoxide-releasing compound. In one embodiment, the pharmaceutical composition is administered by an artificial lung. In one embodiment, the pharmaceutical composition is administered by an extracorporeal membrane gas exchange device.

In yet another aspect, methods of ameliorating age-related damage to DNA in a patient are provided. The methods include administering to the patient a pharmaceutical composition comprising an amount of carbon monoxide effective to ameliorate age-related damage to DNA in the patient.

In one embodiment, the the pharmaceutical composition is in gaseous form and is administered to the patient by inhalation. In one embodiment, the pharmaceutical composition is in liquid form and is administered to the patient orally. In one embodiment, the pharmaceutical composition is administered directly to the abdominal cavity of the patient. In one embodiment, the pharmaceutical composition comprises a carbon monoxide-releasing compound. In one embodiment, the pharmaceutical composition is administered by an artificial lung. In one embodiment, the pharmaceutical composition is administered by an extracorporeal membrane gas exchange device.

The subject or patient can be an animal, human or non-human. For example, the patient can be any mammal, e.g., humans, other primates, pigs, rodents such as mice and rats, rabbits, guinea pigs, hamsters, cows, horses, cats, dogs, sheep and goats. The DNA damage can be the result of, or a person may be considered at risk for DNA damage because of, any of a number of factors. The pharmaceutical composition can be in any form, e.g., gaseous or liquid form.

The pharmaceutical composition can be administered to the patient by any method known in the art for administering gases and/or liquids to patients, e.g., via inhalation, insufflation, infusion, injection, and/or ingestion. In one embodiment of the present invention, the pharmaceutical composition is administered to the patient by inhalation. In another embodiment, the pharmaceutical composition is administered to the patient orally. In still another embodiment, the pharmaceutical composition is administered directly to the abdominal cavity of the patient. In yet another embodiment, the pharmaceutical composition is administered by an artificial lung or an extracorporeal membrane gas exchange device.

The present disclosure also features methods of treating, preventing, or reducing the risk of, DNA damage in a patient. The methods include identifying a patient diagnosed as suffering from or at risk for DNA damage (e.g., a patient diagnosed as suffering from or at risk for DNA damage), and administering to the patient a pharmaceutical composition comprising an amount of carbon monoxide effective to treat DNA damage in the patient.

The present disclosure also features methods of inhibiting or reducing aging or cellular senescence in a patient. The method include identifying a patient in need of inhibition or reduction of aging or cellular senescence and administering to the patient a pharmaceutical composition comprising an effective amount of carbon monoxide.

In another embodiment, the method further includes administering to the patient at least one of the following treatments: inducing HO-1 or ferritin in the patient; expressing recombinant HO-1 or ferritin in the patient; and administering a pharmaceutical composition comprising HO-1, bilirubin, biliverdin, ferritin, or apoferritin, iron, desferoxamine, or iron dextran to the patient. Also contemplated is use of CO and any of the above-listed agents in the preparation of a medicament for treatment or prevention of DNA damage.

In another aspect, the invention features a method of treating or preventing DNA damage in a patient, which includes identifying a patient suffering from or at risk for DNA damage (e.g., a patient diagnosed as suffering from or at risk for DNA damage), providing a vessel containing a pressurized gas comprising carbon monoxide gas, releasing the pressurized gas from the vessel to form an atmosphere comprising carbon monoxide gas, and exposing the patient to the atmosphere, wherein the amount of carbon monoxide in the atmosphere is sufficient to treat DNA damage in the patient.

Also contemplated is use of CO in the preparation of a medicament, e.g., a gaseous or liquid medicament, for use in the treatment or prevention of DNA damage.

Also within the invention is the use of CO in the manufacture of a medicament for treatment or prevention of DNA damage. The medicament can be used in a method for treating DNA damage in a patient suffering from or at risk for DNA damage in accordance with the methods described herein. The medicament can be in any form described herein, e.g., a liquid, solid (CO-releasing compound tablet, enema, etc.), or gaseous CO composition.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

The details of one or more embodiments of the invention are set forth in the description below. Other features, objects, and advantages of the invention will be apparent from the description and the claims.

BRIEF DESCRIPTION OF THE DRAWINGS

FIGS. 6A-F are a panel of photomicrographs and bar graphs showing CO blocks DNA damage in tissues of mice treated with doxorubicin. A-E. A series of 15 photomicrographs of immunoblots with antibody against H2AXγ in colon (A), kidney (B), lung (C), liver (D), and spleen (E). Magnification 20× for colon and kidney; magnification 40× for spleen, liver, lung. #p<0.05, doxorubicin versus control; *p<0.05 CO+doxorubicin versus Air+doxorubicin; **p<0.001 CO+doxorubicin versus Air+doxorubicin. F. A bar graph depicting quantitation of H2AXγ staining in the tissues. Control (Air or CO), n=3, Doxorubicin±CO, n=5. Averages±SD of number of H2AXγ positive cells per FOV are presented.

DETAILED DESCRIPTION

Figures 1A, 1B, 1C:
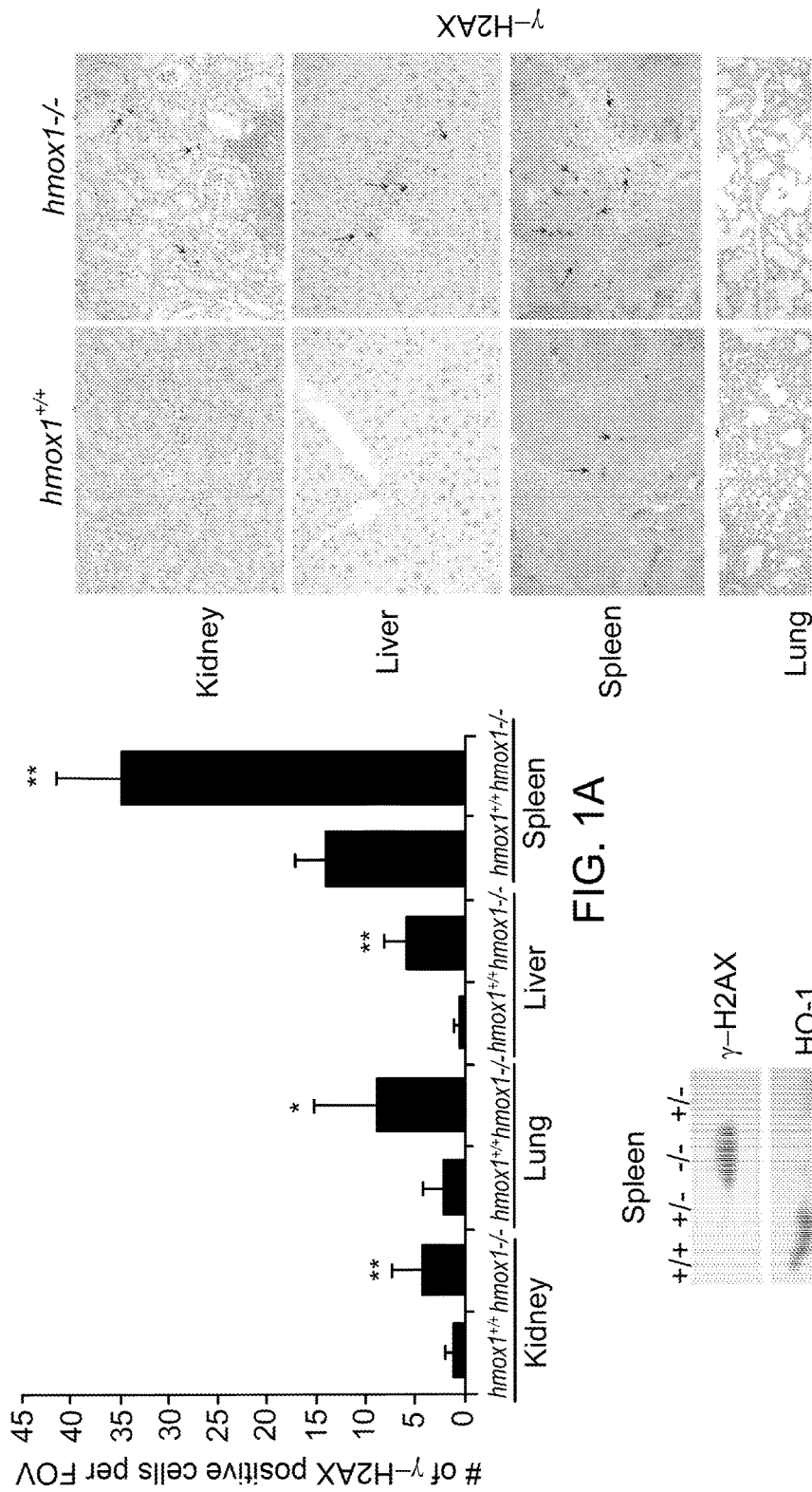
FIGS. 1A-C are a panel of three figures showing the levels of H2AXγ in tissues from hmox1$^{-/-}$ mice. A-B. An immunohistochemical analysis of H2AXγ in kidney, lung, liver, and spleen of wild type (Hmox1$^{+/+}$) and Hmox1$^{-/-}$ mice. C. An immunoblot with antibodies against H2AXγ and HO-1 in the spleen lysates of wild type (+/+), Hmox1$^{-/+}$ (+/−) and Hmox1$^{-/-}$ (−/−) mice. Representative Western blot is shown out of two experiments.

The present invention is based, in part, on the discovery that CO administration ameliorates DNA damage.

The term "carbon monoxide" (or "CO") as used herein describes molecular carbon monoxide in its gaseous state, compressed into liquid form, or dissolved in aqueous solution. The terms "carbon monoxide composition" and "pharmaceutical composition comprising carbon monoxide" is used throughout the specification to describe a gaseous, solid, or liquid composition containing carbon monoxide that can be administered to a patient and/or an organ by routes including orally, intravenously, subcutaneously, intramuscularly, and topically. The skilled practitioner will recognize which form of the pharmaceutical composition, e.g., gaseous, liquid, or both gaseous and liquid forms, is preferred for a given application.

The terms "effective amount" and "effective to treat," as used herein, refer to an amount or concentration of carbon monoxide utilized for period of time (including acute or chronic administration and periodic or continuous administration) that is effective within the context of its administration for causing an intended effect or physiological outcome. Effective amounts of carbon monoxide for use in the present invention include, for example, amounts that prevent DNA damage, reduce the risk of DNA damage, reduce the symptoms of DNA damage, improve the outcome of genotoxic treatments, extend life, increase life span, and/or prevent aging.

For gases, effective amounts of carbon monoxide generally fall within the range of about 0.0000001% to about 0.3% by weight, e.g., 0.0001% to about 0.25% by weight, preferably at least about 0.001%, e.g., at least 0.005%, 0.010%, 0.02%, 0.025%, 0.03%, 0.04%, 0.05%, 0.06%, 0.08%, 0.10%, 0.15%, 0.20%, 0.22%, or 0.24% by weight carbon monoxide. Preferred ranges include, e.g., 0.001% to about 0.24%, about 0.005% to about 0.22%, about 0.005% to about 0.05%, about 0.010% to about 0.20%, about 0.02% to about 0.15%, about 0.025% to about 0.10%, or about 0.03% to about 0.08%, or about 0.04% to about 0.06%. For liquid solutions of CO, effective amounts generally fall within the range of about 0.0001 to about 0.0044 g CO/100 g liquid, e.g., at least 0.0001, 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. A skilled practitioner will appreciate that amounts outside of these ranges may be used, depending upon the application. The skilled practitioner will also appreciate that amounts of CO derived from a CO-RM or CO-Hb that would achieve the same doses in the body when given as a gas can be administered.

The term and "subject" and "patient" are used interchangeably throughout the specification to describe an animal, human or non-human, to whom treatment according to the methods of the present invention is provided. Veterinary applications are contemplated by the present invention. The term includes but is not limited to mammals, e.g., humans, other primates, pigs, rodents such as mice and rats, rabbits, guinea pigs, hamsters, cows, horses, cats, dogs, sheep and goats. The term "treat(ment)," is used herein to describe delaying the onset of, inhibiting, or alleviating the effects of a condition, e.g., DNA damage, in a patient.

The term "DNA damage" is an art-recognized term and is used herein to refer to chemical changes to DNA, e.g., damaged (oxidized, alkylated, hydrolyzed, adducted, or cross-linked) bases, single-stranded DNA breaks, and double-stranded DNA breaks.

Causative agents of DNA damage include, for example, ultraviolet light, ionizing radiation (X-rays, gamma rays, alpha particles), aging and aging-related disorders (e.g., Hutchinson-Gilford Progeria Syndrome, Werner's syndrome, Cockayne's syndrome, or xeroderma pigmentosum), and genotoxic or mutagenic agents, e.g., reactive oxygen species, base analogs, deaminating agents (e.g., nitrous acid), intercalating agents (e.g., ethidium bromide), alkylating agents (e.g., ethylnitrosourea), alkaloids (e.g., Vinca alkaloids), bromines, sodium azide, psoralen, and benzene. Exemplary genotoxic agents used in cancer therapy include busulfan, bendamustine, carboplatin, carmustine, chlorambucil, cisplatin, cyclophosphamide, dacarbazine, daunorubicin, decitabine, doxorubicin, epirubicin, etoposide, idarubicin, ifosfamide, irinotecan, lomustine, mechlorethamine, melphalan, mitomycin C, mitoxantrone, oxaliplatin, temozolomide, and topotecan.

In some cases, a subject or patient suffering from or at risk for DNA damage has been exposed to or is likely to be exposed to ionizing radiation, e.g., at an acute dose of at least or about 0.1 Gy, e.g., at least or about 0.2 Gy, at least or about 0.5 Gy, at least or about 1 Gy, at least or about 2 Gy, at least or about 4 Gy, at least or about 5 Gy, at least or about 6 Gy, at least or about 7 Gy, at least or about 8 Gy, at least or about 10 Gy, at least or about 20 Gy, at least or about 30 Gy, at least or about 40 Gy, at least or about 50 Gy, or at least or about 100 Gy. Skilled practitioners will appreciate what levels of radiation damage DNA. In some cases, a subject will be, is being, or has been exposed to DNA-damaging levels of radiation, e.g., at least or about 0.1 Gy, e.g., at least or about 0.2 Gy, at least or about 0.5 Gy, at least or about 1 Gy, at least or about 2 Gy, at least or about 4 Gy, at least or about 5 Gy, at least or about 6 Gy, at least or about 7 Gy, at least or about 8 Gy, at least or about 10 Gy, at least or about 20 Gy, at least or about 30 Gy, at least or about 40 Gy, at least or about 50 Gy, or at least or about 100 Gy. The subject can be exposed to DNA-damaging levels of radiation through their occupation, e.g., a health care worker, miner, nuclear energy worker, and airline crew member, from a nuclear reactor, or from nuclear weapon, e.g., during warfare and/or an act of terrorism. The pharmaceutical composition can be administered before, while, and/or after the subject has been exposed to DNA-damaging levels of radiation.

In some cases, a patient suffering from or at risk for DNA damage will be suffering from a burn. A patient suffering from or at risk for DNA damage can be one undergoing one or more genotoxic treatments, e.g., chemotherapy with a genotoxic agent, radiotherapy, or hyperthermia therapy. A patient suffering from or at risk for DNA damage may have a deleterious genetic defect or mutation. In some cases, the present methods ameliorate age-related damage to DNA in a patient.

In some cases, aging is a consequence of unrepaired DNA damage accumulation. Age-related damage to DNA results in DNA alteration that has an abnormal structure. Although both mitochondrial and nuclear DNA damage can contribute to aging, nuclear DNA is the main subject of this analysis. Nuclear DNA damage can contribute to aging either indirectly (by increasing apoptosis or cellular senescence) or directly (by increasing cell dysfunction).

In humans, DNA damage occurs frequently, and DNA repair processes have evolved to compensate. On average, approximately 800 DNA lesions occur per hour in each cell, or about 19,200 per cell per day. In any cell, some DNA damage may remain despite the action of repair processes. Accumulation of unrepaired DNA damage is more prevalent in certain types of cells, particularly in non-replicating or slowly replicating cells, which cannot rely on DNA repair mechanisms associated with DNA replication such as those in the brain, skeletal, and cardiac muscle. Older patients, e.g., at least or about 30 years old, at least or about 35 years old, at least or about 40 years old, at least or about 45 years old, at least or about 50 years old, at least or about 55 years old, at least or about 60 years old, at least or about 65 years old, at least or about 70 years old, at least or about 75 years old, or at least or about 80 years old, typically accumulate more age-related damage to DNA and can benefit from treatment to ameliorate age-related damage to DNA.

Skilled practitioners will appreciate that a patient can be diagnosed by a physician as suffering from or at risk for DNA damage by any method known in the art. Individuals considered at risk for developing DNA damage may benefit particularly from the invention, primarily because prophylactic treatment can begin before there is any evidence of DNA damage. Individuals "at risk" include, e.g., subjects exposed to environmental, occupational, or therapeutic genotoxic agents. The skilled practitioner will appreciate that a patient can be determined to be at risk for DNA damage by a physician's diagnosis.

Amounts of CO effective to treat DNA damage can be administered to a patient on the day the patient is diagnosed as suffering from DNA damage or any condition associated with DNA damage, or as having any risk factor associated with an increased likelihood that the patient will develop DNA damage (e.g., that the patient has recently been, is being, or will be exposed to a genotoxic agent). Patients can inhale CO at concentrations ranging from 10 ppm to 1000 ppm, e.g., about 100 ppm to about 800 ppm, about 150 ppm to about 600 ppm, or about 200 ppm to about 500 ppm. Preferred concentrations include, e.g., about 30 ppm, 50 ppm, 75 ppm, 100 ppm, 125 ppm, 200 ppm, 250 ppm, 500 ppm, 750 ppm, or about 1000 ppm. CO can be administered to the patient intermittently or continuously. CO can be administered for about 1, 2, 4, 6, 8, 10, 12, 14, 18, or 20 days, or greater than 20 days, e.g., 1 2, 3, 5, or 6 months, or until the patient no longer exhibits symptoms of DNA damage, or until the patient is diagnosed as no longer being at risk for DNA damage. In a given day, CO can be administered continuously for the entire day, or intermittently, e.g., a single whiff of CO per day (where a high concentration is used), or for up to 23 hours per day, e.g., up to 20, 15, 12, 10, 6, 3, or 2 hours per day, or up to 1 hour per day. A dosage of CO administered can be converted mathematically to a mg/kg dosing based on time and concentration of administration and a patient's body weight.

If the patient needs to be treated with a genotoxic drug (e.g., because prescribed by a physician), the patient can be treated with CO (e.g., a gaseous CO composition) before, during, and/or after administration of the drug. For example, CO can be administered to the patient, intermittently or continuously, starting 0 to 20 days before the drug is administered (and where multiple doses are given, before each individual dose), e.g., starting at least about 30 minutes, e.g., about 1, 2, 3, 5, 7, or 10 hours, or about 1, 2, 4, 6, 8, 10, 12, 14, 18, or 20 days, or greater than 20 days, before the administration. Alternatively or in addition, CO can be administered to the patient concurrent with administration of the drug. Alternatively or in addition, CO can be administered to the patient after administration of the drug, e.g., starting immediately after administration, and continuing intermittently or continuously for about 1, 2, 3, 5, 7, or 10 hours, or about 1, 2, 5, 8, 10, 20, 30, 50, or 60 days, indefinitely, or until a physician determines that administration of CO is no longer necessary (e.g., after the genotoxic agent is eliminated from the body or can no longer cause DNA damage).

Administration of CO is further described in U.S. Pat. No. 7,238,469; U.S. Pat. No. 7,678,390; U.S. Pat. No. 7,687,079; U.S. Pat. No. 7,981,448; U.S. Pat. No. 7,364,757; U.S. 2004/0258772; U.S. 2004/0052866; U.S. 2004/0228930; and U.S. 2004/131703, each of which is incorporated by reference herein in its entirety.

Preparation of Gaseous Compositions

A carbon monoxide composition may be a gaseous carbon monoxide composition. Compressed or pressurized gas useful in the methods of the invention can be obtained from any commercial source and in any type of vessel appropriate for storing compressed gas. For example, compressed or pressurized gases can be obtained from any source that supplies compressed gases, such as oxygen, for medical use. The term "medical grade" gas, as used herein, refers to gas suitable for administration to patients as defined herein. The pressurized gas including CO used in the methods of the present invention can be provided such that all gases of the desired final composition (e.g., CO, He, NO, $CO_2$, $O_2$, $N_2$) are in the same vessel, except that NO and $O_2$ cannot be stored together. Optionally, the methods of the present invention can be performed using multiple vessels containing individual gases. For example, a single vessel can be provided that contains carbon monoxide, with or without other gases, the contents of which can be optionally mixed with room air or with the contents of other vessels, e.g., vessels containing oxygen, nitrogen, carbon dioxide, compressed air, or any other suitable gas or mixtures thereof.

Gaseous compositions administered to a patient according to the present invention typically contain 0% to about 79% by weight nitrogen, about 21% to about 100% by weight oxygen and about 0.0000001% to about 0.3% by weight (corresponding to about 1 ppb or 0.001 ppm to about 3,000 ppm) carbon monoxide. Preferably, the amount of nitrogen in the gaseous composition is about 79% by weight, the amount of oxygen is about 21% by weight and the amount of carbon monoxide is about 0.0001% to about 0.25% by weight, preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight. Preferred ranges of carbon monoxide include about 0.005% to about 0.24%, about 0.01% to about 0.22%, about 0.015% to about 0.20%, about 0.08% to about 0.20%, and about 0.025% to about 0.1% by weight. It is noted that gaseous carbon monoxide compositions having concentrations of carbon monoxide greater than 0.3% (such as 1% or greater) may be used for short periods (e.g., one or a few breaths), depending upon the application.

A gaseous carbon monoxide composition may be used to create an atmosphere that comprises carbon monoxide gas. An atmosphere that includes appropriate levels of carbon monoxide gas can be created, for example, by providing a vessel containing a pressurized gas comprising carbon monoxide gas, and releasing the pressurized gas from the vessel into a chamber or space to form an atmosphere that includes the carbon monoxide gas inside the chamber or space. Alternatively, the gases can be released into an apparatus that culminates in a breathing mask or breathing tube, thereby creating an atmosphere comprising carbon monoxide gas in the breathing mask or breathing tube, ensuring the patient is the only person in the room exposed to significant levels of carbon monoxide.

Carbon monoxide levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026-2032, 1982; Ingi et al., Neuron 16:835-842, 1996). Sub-parts per million carbon monoxide levels can be detected by, e.g., gas chromatography and radioisotope counting. Further, it is known in the art that carbon monoxide levels in the sub-ppm range can be measured in biological tissue by a midinfrared gas sensor (see, e.g., Morimoto et al., Am. J. Physiol. Heart. Circ. Physiol 280:H482-H488, 2001). Carbon monoxide sensors and gas detection devices are widely available from many commercial sources.

Preparation of Liquid Compositions

A carbon monoxide composition may also be a liquid carbon monoxide composition. A liquid can be made into a carbon monoxide composition by any method known in the art for causing gases to become dissolved in liquids. For example, the liquid can be placed in a so-called "$CO_2$ incubator" and exposed to a continuous flow of carbon monoxide, preferably balanced with carbon dioxide, until a desired concentration of carbon monoxide is reached in the liquid. As another example, carbon monoxide gas can be "bubbled" directly into the liquid until the desired concentration of carbon monoxide in the liquid is reached. The amount of carbon monoxide that can be dissolved in a given aqueous solution increases with decreasing temperature. As still another example, an appropriate liquid may be passed through tubing that allows gas diffusion, where the tubing runs through an atmosphere comprising carbon monoxide (e.g., utilizing a device such as an extracorporeal membrane oxygenator). The carbon monoxide diffuses into the liquid to create a liquid carbon monoxide composition.

It is likely that such a liquid composition intended to be introduced into a living animal will be at or about 37° C. at the time it is introduced into the animal.

The liquid can be any liquid known to those of skill in the art to be suitable for administration to patients (see, for example, Oxford Textbook of Surgery, Morris and Malt, Eds., Oxford University Press (1994)). In general, the liquid will be an aqueous solution. Examples of solutions include Phosphate Buffered Saline (PBS), Celsior™, Perfadex™, Collins solution, citrate solution, and University of Wisconsin (UW) solution (Oxford Textbook of Surgery, Morris and Malt, Eds., Oxford University Press (1994)). In one embodiment of the present invention, the liquid is Ringer's Solution, e.g., lactated Ringer's Solution, or any other liquid that can be used infused into a patient. In another embodiment, the liquid includes blood, e.g., whole blood.

Any suitable liquid can be saturated to a set concentration of carbon monoxide via gas diffusers. Alternatively, premade solutions that have been quality controlled to contain set levels of carbon monoxide can be used. Accurate control of dose can be achieved via measurements with a gas permeable, liquid impermeable membrane connected to a carbon monoxide analyzer. Solutions can be saturated to desired effective concentrations and maintained at these levels.

Treatment of Patients with Carbon Monoxide Compositions

A patient can be treated with a carbon monoxide composition by any method known in the art of administering gases and/or liquids to patients. Carbon monoxide compositions can be administered to a patient diagnosed with, or determined to be at risk for, DNA damage. The present invention contemplates the systemic administration of liquid or gaseous carbon monoxide compositions to patients (e.g., by inhalation and/or ingestion), and the topical administration of the compositions to the patient (e.g., by introduction into the abdominal cavity).

Systemic Delivery of Carbon Monoxide

Gaseous carbon monoxide compositions can be delivered systemically to a patient, e.g., a patient diagnosed with, or determined to be at risk for DNA damage. Gaseous carbon monoxide compositions are typically administered by inhalation through the mouth or nasal passages to the lungs, where the carbon monoxide is readily absorbed into the patient's bloodstream. The concentration of active compound (CO) utilized in the therapeutic gaseous composition will depend on absorption, distribution, inactivation, and excretion (generally, through respiration) rates of the carbon monoxide as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. Treatments can be monitored and CO dosages can be adjusted to ensure optimal treatment of the patient. Acute, sub-acute and chronic administration of carbon monoxide is contemplated by the present invention, depending upon, e.g., the severity or persistence of DNA damage in the patient. Carbon monoxide can be delivered to the patient for a time (including indefinitely) sufficient to treat the condition and exert the intended pharmacological or biological effect.

The following are examples of some methods and devices that can be utilized to administer gaseous carbon monoxide compositions to patients.

Ventilators

Medical grade carbon monoxide (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration in ppm (parts per million). The patient will inhale the gas mixture through a ventilator, which will be set to a flow rate based on patient comfort and needs. This is determined by pulmonary graphics (i.e., respiratory rate, tidal volumes etc.). Fail-safe mechanism(s) to prevent the patient from unnecessarily receiving greater than desired amounts of carbon monoxide can be designed into the delivery system. The patient's carbon monoxide level can be monitored by studying (1) carboxyhemoglobin (COHb), which can be measured in venous blood, and (2) exhaled carbon monoxide collected from a side port of the ventilator. Carbon monoxide exposure can be adjusted based upon the patient's health status and on the basis of the markers. If necessary, carbon monoxide can be washed out of the patient by switching to 100% $O_2$ inhalation. Carbon monoxide is not metabolized; thus, whatever is inhaled will ultimately be exhaled except for a very small percentage that is converted to $CO_2$. Carbon monoxide can also be mixed with any level of $O_2$ to provide therapeutic delivery of carbon monoxide without consequential hypoxic conditions.

Face Mask and Tent

A carbon monoxide-containing gas mixture is prepared as above to allow passive inhalation by the patient using a facemask or tent. The concentration inhaled can be changed and can be washed out by simply switching over to 100% $O_2$. Monitoring of carbon monoxide levels would occur at or near the mask or tent with a fail-safe mechanism that would prevent too high of a concentration of carbon monoxide from being inhaled.

Portable Inhaler

Compressed carbon monoxide can be packaged into a portable inhaler device and inhaled in a metered dose, for example, to permit intermittent treatment of a recipient who is not in a hospital setting. Different concentrations of carbon monoxide could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for carbon monoxide delivery. The catheter, when implanted, resides in one of the large veins and would be able to deliver carbon monoxide at given concentrations either for systemic delivery or at a local site. The delivery can be a local delivery of a high concentration of carbon monoxide for a short period of time at the site of the procedure (this high concentration would rapidly be diluted out in the bloodstream), or a relatively longer exposure to a lower concentration of carbon monoxide (see, e.g., Hattler et al., Artif. Organs 18(11):806-812 (1994); and Golob et al., ASAIO J., 47(5):432-437 (2001)).

Normobaric Chamber

In certain instances, it may be desirable to expose the whole patient to carbon monoxide. The patient would be inside an airtight chamber that would be flooded with carbon monoxide (at a level that does not endanger the patient, or at a level that poses an acceptable risk without the risk of bystanders being exposed. Upon completion of the exposure, the chamber could be flushed with air (e.g., 21% $O_2$, 79% $N_2$) and samples could be analyzed by carbon monoxide analyzers to ensure no carbon monoxide remains before allowing the patient to exit the exposure system.

Systemic Delivery of Liquid CO Compositions

The present invention further contemplates that aqueous solutions comprising carbon monoxide can be created for systemic delivery to a patient, e.g., for oral delivery and/or by infusion into the patient, e.g., intravenously, intra-arterially, intraperitoneally, and/or subcutaneously. For example, liquid CO compositions, such as CO-saturated Ringer's Solution, can be infused into a patient suffering from or at risk for DNA damage. Alternatively or in addition, CO-partially or completely saturated whole (or partial) blood can be infused into the patient. CO can also be administered as a CO-RM or CO-saturated Hb (artificial, e.g. pegylated or non-pegylated; also could be any formulation of Hb that can be saturated with CO and then infused into the patient.)

The present invention also contemplates that agents capable of delivering doses of gaseous CO compositions or liquid CO compositions can be utilized (e.g., CO-releasing gums, creams, ointments, lozenges, or patches).

Topical Treatment of Organs with Carbon Monoxide

Alternatively or in addition, carbon monoxide compositions can be applied directly to an organ, or to any portion thereof, to ameliorate DNA damage. A gaseous composition can be directly applied to an organ of a patient by any method known in the art for insufflating gases into a patient. For example, gases, e.g., carbon dioxide, are often insufflated into the abdominal cavity of patients to facilitate examination during laproscopic procedures (see, e.g., Oxford Textbook of Surgery, Morris and Malt, Eds., Oxford University Press (1994)). The skilled practitioner will appreciate that similar procedures could be used to administer carbon monoxide compositions directly to an organ of a patient.

Aqueous carbon monoxide compositions can also be administered topically to an organ of a patient to ameliorate DNA damage. Aqueous forms of the compositions can be administered by any method known in the art for administering liquids to patients. As with gaseous compositions, aqueous compositions can be applied directly to the organ. For example, liquids, e.g., saline solutions containing dissolved CO, can be injected into the abdominal cavity of patients during laproscopic procedures. The skilled practitioner will appreciate that similar procedures could be used to administer liquid carbon monoxide compositions directly to an organ of a patient. Further, an in situ exposure can be carried out by flushing the organ or a portion thereof with a liquid carbon monoxide composition (see Oxford Textbook of Surgery, Morris and Malt, Eds., Oxford University Press (1994)).

Use of Heme Oxygenase-1, Other Compounds, and Other Treatments for DNA Damage

Also contemplated by the present invention is the induction or expression of heme oxygenase-1 (HO-1) in conjunction with administration of CO. For example, HO-1 can be induced in a patient suffering from or at risk for DNA damage. As used herein, the term "induce(d)" means to cause increased production of a protein, e.g., HO-1, in isolated cells or the cells of a tissue, organ or animal using the cells' own endogenous (e.g., non-recombinant) gene that encodes the protein.

HO-1 can be induced in a patient by any method known in the art. For example, production of HO-1 can be induced by hemin/heme arginate, by iron protoporphyrin, or by cobalt protoporphyrin. A variety of non-heme agents including heavy metals, cytokines, hormones, NO, $COCl_2$, endotoxin and heat shock are also strong inducers of HO-1 expression (Choi et al., Am. J. Respir. Cell Mol. Biol. 15:9-19, 1996; Maines, Annu Rev. Pharmacol. Toxicol. 37:517-554, 1997; and Tenhunen et al., J. Lab. Clin. Med. 75:410-421, 1970). HO-1 is also highly induced by a variety of agents causing oxidative stress, including hydrogen peroxide, glutathione depletors, UV irradiation, endotoxin and hyperoxia (Choi et al., Am. J. Respir. Cell Mol. Biol. 15:9-19, 1996; Maines, Annu Rev. Pharmacol. Toxicol. 37:517-554, 1997; and Keyse et al., Proc. Natl. Acad. Sci. USA 86:99-103, 1989). A "pharmaceutical composition comprising an inducer of HO-1" means a pharmaceutical composition containing any agent capable of inducing HO-1 in a patient, e.g., any of the agents described above, e.g., NO, hemin, iron protoporphyrin, and/or cobalt protoporphyrin.

HO-1 expression in a cell can be increased via gene transfer. As used herein, the term "express(ed)" means to cause increased production of a protein, e.g., HO-1 or ferritin, in isolated cells or the cells of a tissue, organ or animal using an exogenously administered gene (e.g., a recombinant gene). The HO-1 or ferritin is preferably of the same species (e.g., human, mouse, rat, etc.) as the recipient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retrovirus, adenovirus, adeno-associated virus (AAV), pox (e.g., vaccinia) virus, human immunodeficiency virus (HIV), the minute virus of mice, hepatitis B virus, influenza virus, Herpes Simplex Virus-1, and lentivirus) encoding HO-1 or ferritin would be administered to a patient suffering from or at risk for DNA damage, by mouth, by inhalation, or by injection. Similarly, plasmid vectors encoding HO-1 or apoferritin can be administered, e.g., as naked DNA, in liposomes, or in microparticles.

Further, exogenous HO-1 protein can be directly administered to a patient by any method known in the art. Exogenous HO-1 can be directly administered in addition, or as an alternative, to the induction or expression of HO-1 in the patient as described above. The HO-1 protein can be delivered to a patient, for example, in liposomes, and/or as a fusion protein, e.g., as a TAT-fusion protein (see, e.g., Becker-Hapak et al., Methods 24:247-256, 2001).

Alternatively or in addition, any of the products of metabolism by HO-1, e.g., bilirubin, biliverdin, iron, and/or ferritin, can be administered to a patient in conjunction with CO in order to prevent or treat DNA damage. Further, the present invention contemplates that iron-binding molecules other than ferritin, e.g., desferoxamine (DFO), iron dextran, and/or apoferritin, can be administered to the patient. Further still, the present invention contemplates that enzymes (e.g., biliverdin reductase) that catalyze the breakdown any of these products can be inhibited to create/enhance the desired effect. Any of the above can be administered, e.g., orally, intravenously, intraperitoneally, or by direct administration.

The present invention contemplates that compounds that release CO into the body after administration of the compound (e.g., CO-releasing compounds, e.g., photoactivatable CO-releasing compounds), e.g., dimanganese decacarbonyl, tricarbonyldichlororuthenium (II) dimer, and methylene chloride (e.g., at a dose of between 400 to 600 mg/kg, e.g., about 500 mg/kg), can also be used in the methods of the present invention, as can carboxyhemoglobin and CO-donating hemoglobin substitutes. See, e.g., U.S. 2003/0064114, U.S. 2003/0068387, and U.S. 2007/0207217.

The above can be administered to a patient in any way, e.g., by oral, intraperitoneal, intravenous, or intraarterial administration as well as topical (including sublingual and suppository) as well as an aerosol to the lungs. Any of the above compounds can be administered to the patient locally and/or systemically, and in any combination.

The present invention further contemplates treating/preventing DNA damage by administering CO to the patient in combination with any other known methods or compounds for treating DNA damage, e.g., cessation or reducing administration of genotoxic agents.

The invention is illustrated in part by the following examples, which are not to be taken as limiting the invention in any way.

EXAMPLES

Example 1. Lack of HO-1 Results in Accumulation of γ-H2AX Foci in Vivo

To evaluate the role of HO-1 in DNA damage and repair signaling, immunohistochemical analyses of γ-H2AX staining, a marker of ongoing and chronic DNA damage, was performed on various tissues harvested from Hmox1$^{-/-}$ mice. A low degree of γ-H2AX was observed in the spleens and lungs of wild type animals and nearly undetectable expression in the kidney and liver (FIGS. 1A-B). In contrast, there was a statistically significant greater amount of γ-H2AX foci in Hmox1$^{-/-}$ animals compared to wild type controls (FIGS. 1A-C). Quantification of the number of H2AXγ foci per field of view (20× magnification; n=3-4, fields n=5-10 from 3-4 mice) is shown in A. Representative pictures are shown in B. *p=0.03, ** p<0.001. Scale bar: 100 μm. These data suggested that either Hmox1$^{-/-}$ cells are unable to repair broken DNA efficiently or the extensive oxidative stress in the tissues of Hmox1$^{-/-}$ mice results in accelerated DNA damage.

Figure 2A:
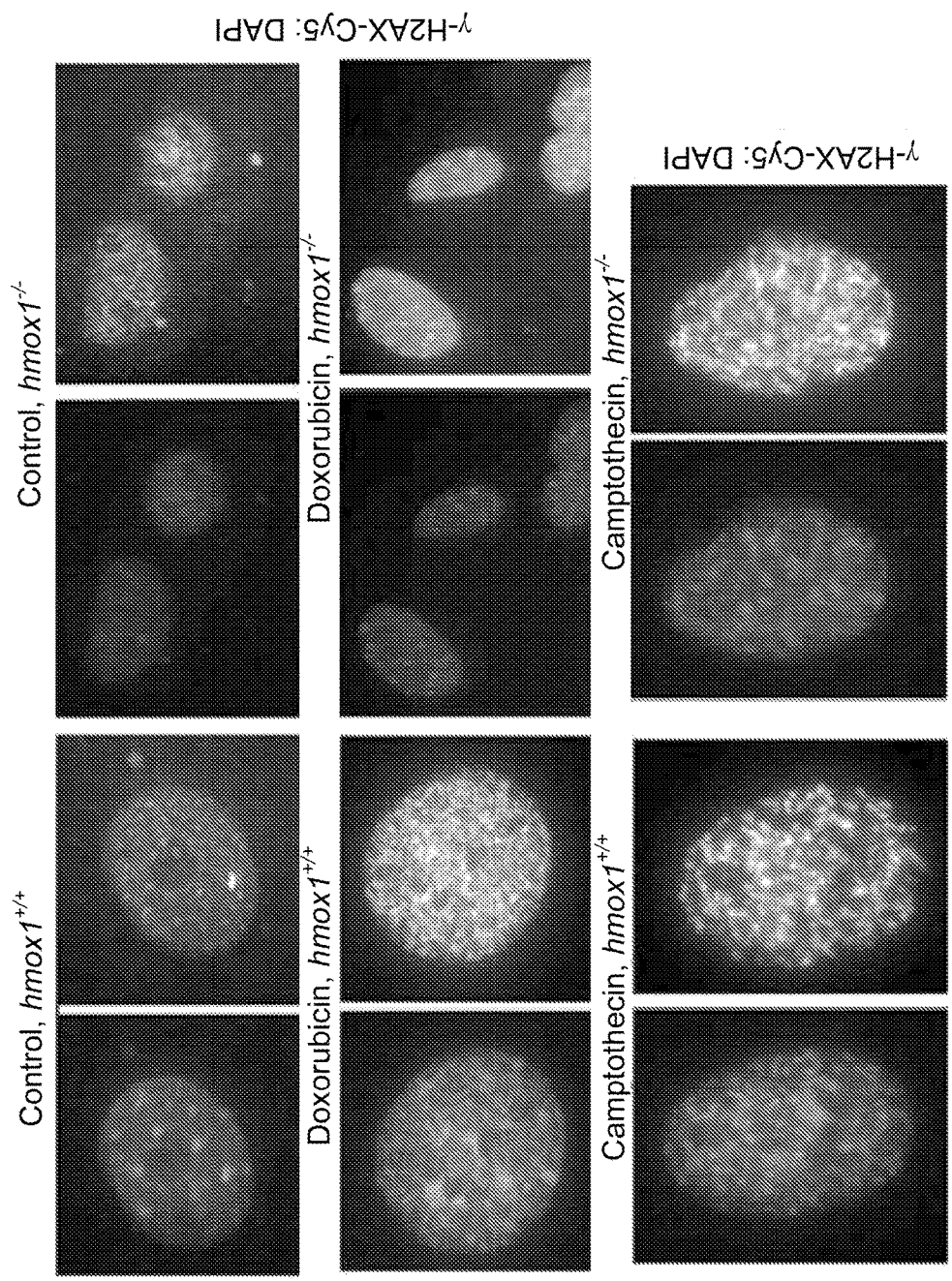
FIGS. 2A-C are a series of three figures depicting a lack of HO-1 results in altered H2AXγ activation in response to DNA damage. A. A panel of photomicrographs showing fibroblasts from Hmox1$^{+/+}$ and Hmox1$^{-/-}$ mice isolated and treated with camptothecin (1 μg/ml) or doxorubicin (10 μg/ml) for 1 hour and stained with antibodies against H2AXγ. Scale bar: 25 μm. B-C. An immunoblot analysis of H2AXγ in the lysates of Hmox1$^{+/+}$, Hmox1$^{-/+}$ and Hmox1$^{-/-}$ fibroblasts that were treated with doxorubicin. Representative figure is shown in B; quantitation is presented in C. Data are representative for at least 2 independent experiments. *p<0.05; 4 hours versus control in Hmox1$^{+/+}$ fibroblasts. # p<0.05; Hmox1$^{-/-}$ versus Hmox1$^{+/+}$.
Figure 2B:
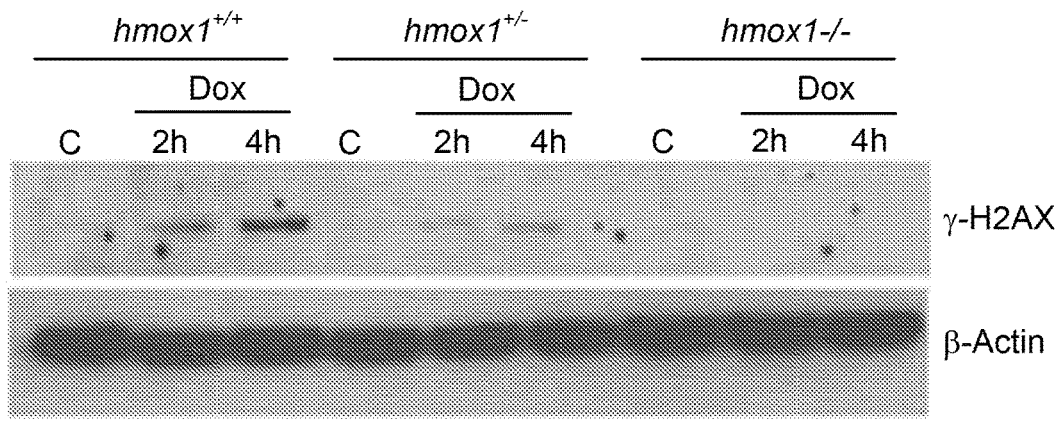
Figure 2C:
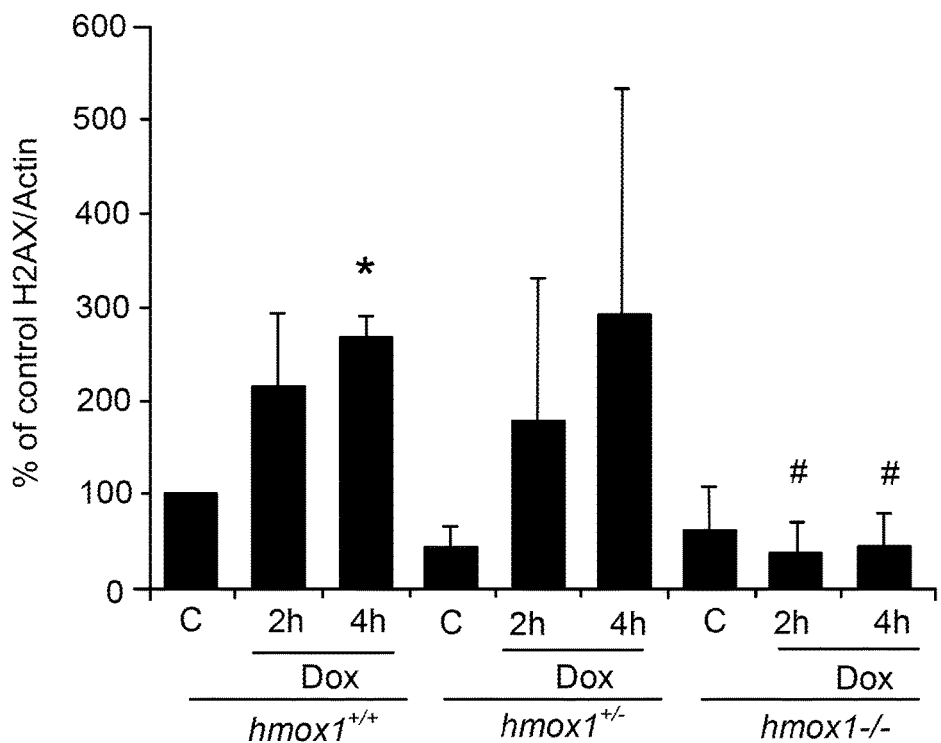

To elucidate whether absence of HO-1 results in accelerated accumulation of DNA damage, cells were treated with doxorubicin or camptothecin, which induce DSB or SSB, respectively, as measured by H2AX phosphorylation (FIG. 2). Treatment of Hmox$^{+/+}$ fibroblasts with doxorubicin or camptothecin resulted in a strong increase in phosphorylation of histone H2AX and formation of multiple γ-H2AX foci (FIGS. 2A-B). Fibroblasts from Hmox1$^{-/-}$ mice also showed similar foci in response to camptothecin as in wild type (FIG. 2A), however in contrast to camptothecin, Hmox1$^{-/-}$ fibroblasts treated with doxorubicin showed no γ-H2AX foci formation or phosphorylation of γ-H2AX at any time point tested which was otherwise present in wild type cells (FIGS. 2A-C). Representative pictures are shown from at least two independent experiments in duplicates. Fibroblasts were treated with doxorubicin (10 μg/ml) for 2-4 hr. These data suggested that HO-1 can mediate DNA repair responses specifically to DSB that are induced by doxorubicin and unlike camptothecin which targets DNA topoisomerase I.

Example 2. Absence of HO-1 Results in Decreased DNA Repair Signaling

Figure 3A:
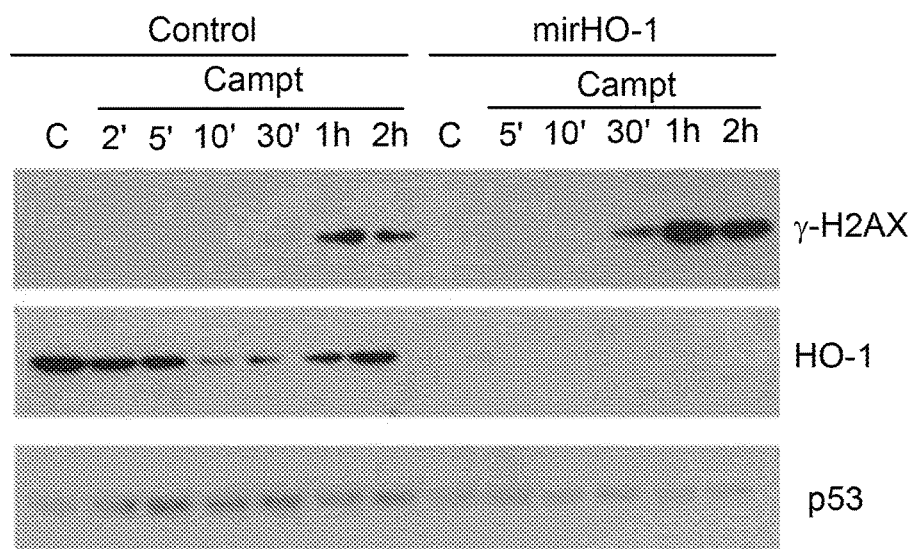
FIGS. 3A-D are a panel of immunoblots showing DNA repair signaling in the absence of HO-1. A-B. HEK293 cells with stable knockdown of HO-1 (mirHO-1) and control cells treated with camptothecin. C. An immunoblot analysis in HEK mirHO-1 and control cells treated with doxorubicin. Data are representative for two experiments. D. An immunoblot analysis with antibodies against P-ATM, P-Brca1, P-H2AX, P-p53 in the lysates of HEK293 mirHO-1 and control cells treated with 10 Gy g-irradiation and harvested 5'-1 h after irradiation. Data are representative for two independent experiments in triplicates.

The direct effects of HO-1 was tested on signaling pathways in response to the DNA damaging agents, doxorubicin, camptothecin, or irradiation in loss and gain of function studies with HO-1. HEK293cells express high basal levels of HO-1 due to presence of large T antigen. HEK293 cells were transduced with micro-adapted shRNA to stably deplete HO-1 and then exposed to camptothecin, doxorubicin or irradiation. HEK293 cells with stable knockdown of HO-1 (mirHO-1) and control cells were treated with camptothecin (1 μg/ml) for 2'-2 h. The levels of HO-1 and DNA repair signaling proteins activation was measured by Western blot. As expected, camptothecin induced phosphorylation of H2AX in wild-type HEK293 cells, which was slightly enhanced in cells without HO-1 (FIG. 3A). These findings correlated with phosphorylation of H2AX observed in the tissues from Hmox1$^{-/-}$ mice (FIG. 1).

Figure 3B:
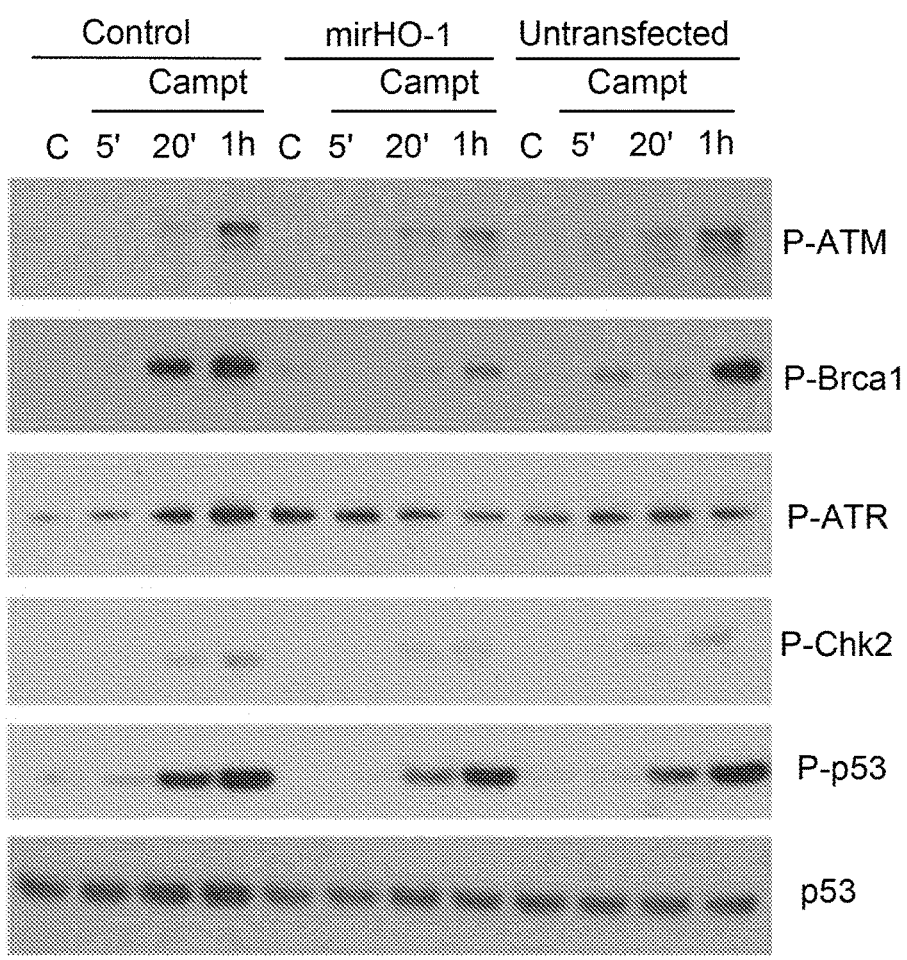

The status of the major DNA repair kinases, ATR, and ATM and their downstream targets was evaluated in HEK293 cells treated with camptothecin. Phosphorylation of ATR, ATM as well as p53, Chk2 and Brca1 were relatively unchanged in stable LMP-infected HEK293 control cells as compared to non-transfected naïve HEK293 cells (FIG. 3B). Knockdown of HO-1 however resulted in a significant decrease in phosphorylation of ATM, Brca1, ATR and Chk2 (FIG. 3B). Importantly, there were no significant changes in phosphorylation of p53, suggesting that HO-1 is specific and important in DNA repair rather than regulating apoptosis or cell cycle progression in the presence of a genotoxic stressor.

Figure 3C:
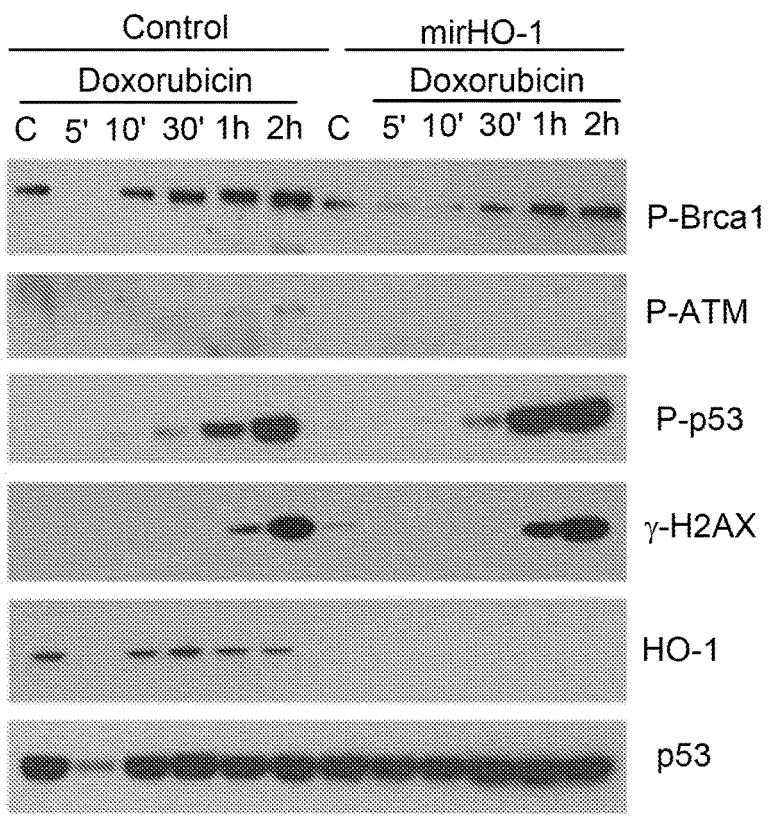
Figure 3D:
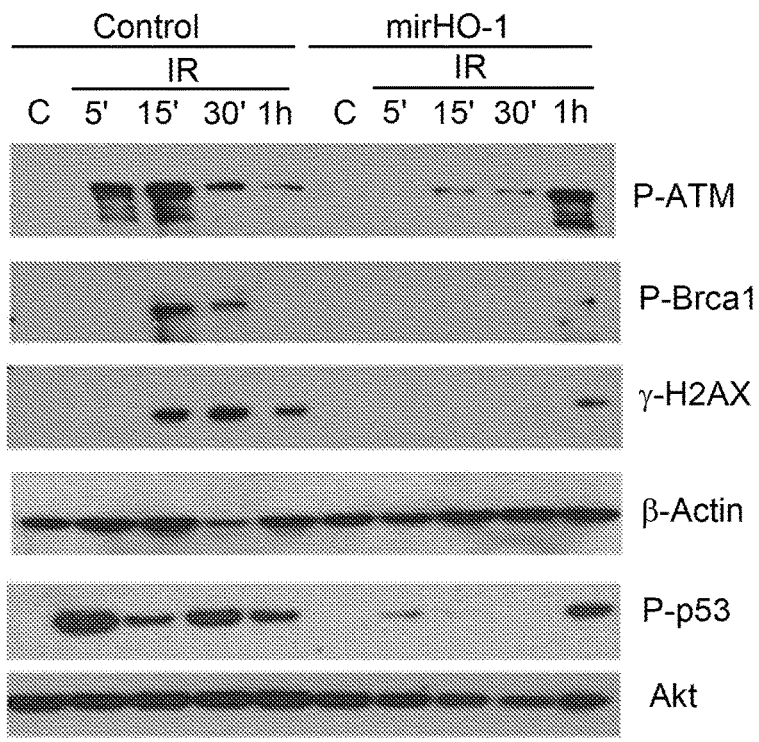

HEK293 cells treated with doxorubicin responded similarly with an increase in phosphorylation of ATM, p53 and H2AX (FIG. 3C). HEK mirHO-1 and control cells treated with doxorubicin (10 μg/ml) for 2'-2 h is shown. Knockdown of HO-1 under these conditions resulted in inhibition in phosphorylated ATM and a delay in Brca1 activation. No significant changes were observed in P-p53 or γ-H2AX in control or mirHO-1-transfected HEK293 cells in the absence of doxorubicin. Further, the effects of irradiation on DNA were investigated in HEK cells in the presence and absence of HO-1 after irradiation (10 Gy). The phosphorylation levels of ATM, Brca1, H2AX and p53 were significantly decreased or delayed in mirHO-1 HEK cells compared to controls (FIG. 3D). There were no significant changes in the total levels of major DNA repair complexes involved in HR-mediated DNA repair in mirHO-1 HEK cells. Akt is a loading control for the immunoblot for P-p53.

Example 3. HO-1/CO Facilitate HR Repair of Double Strand Breaks

Since Hmox1$^{-/-}$ cells showed altered H2AXγ foci formation in response to doxorubicin, and mirHO-1 HEK cells showed diminished activation of major signaling cascades leading to DNA repair in response to camptothecin, the role of HO-1 was assessed in homologous recombination-mediated DNA repair, which is critical in DSB repair induced by doxorubicin or camptothecin (during replication). To test this, the U2OS cell line containing the HR/SCR (homologous recombination/sister chromatid recombination) reporter was used as previously described (12,13). I-SceI endonuclease was used to introduce a double strand break (DSB) within the reporter in U2OS cells. The efficiency of homologous recombination induced by I-SceI correlated with generation of wild type GFP by gene conversion.

Figure 4A:
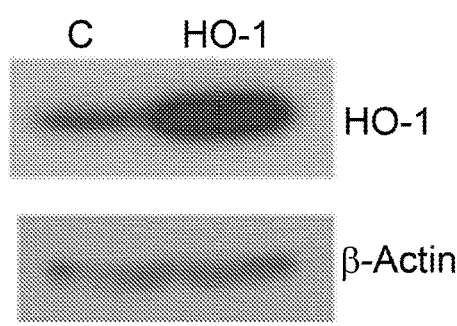
FIGS. 4A-G are a panel of figures showing HO-1/CO induces HR-mediated DNA repair. A. A photomicrograph showing HO-1 levels as measured by Western blot. B-D. A photomicrograph and graphs showing the number of GFP-positive U2OS-SCR reporter cells as measured by fluorescence microscope (B) and flow cytometry (C-D). Data are representative for at least five experiments in duplicate. Data±SD are shown. p<0.05*; CO versus air. Scale bar: 25 µm. E-G. A photomicrograph and graphs showing the level of GFP-positive cells measured by fluorescence microscopy (E) or flow cytometry (F-G). Representative data are shown and are representative for three independent experiments; averages±SD. Scale bar: 25 µm.
Figure 4C:
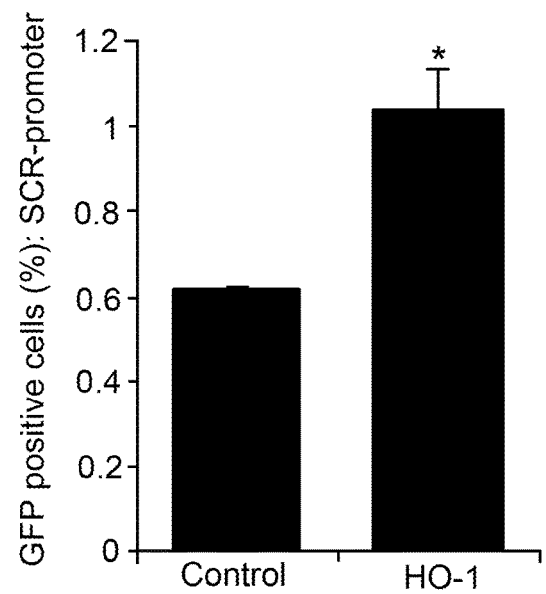
Figure 4B:
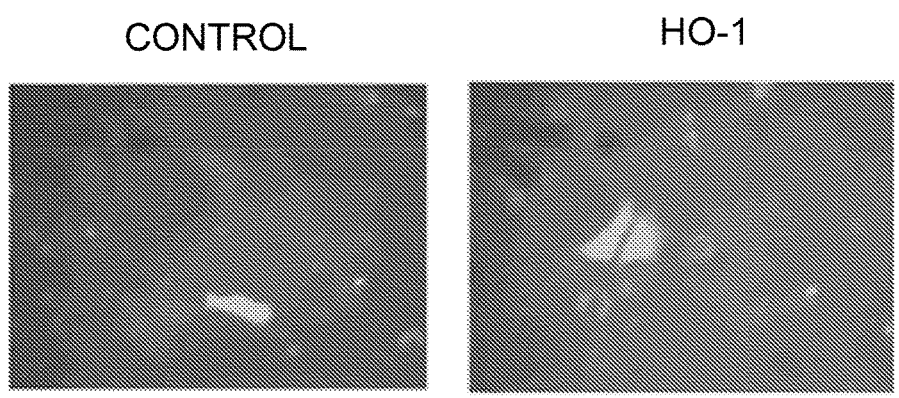
Figure 4D:
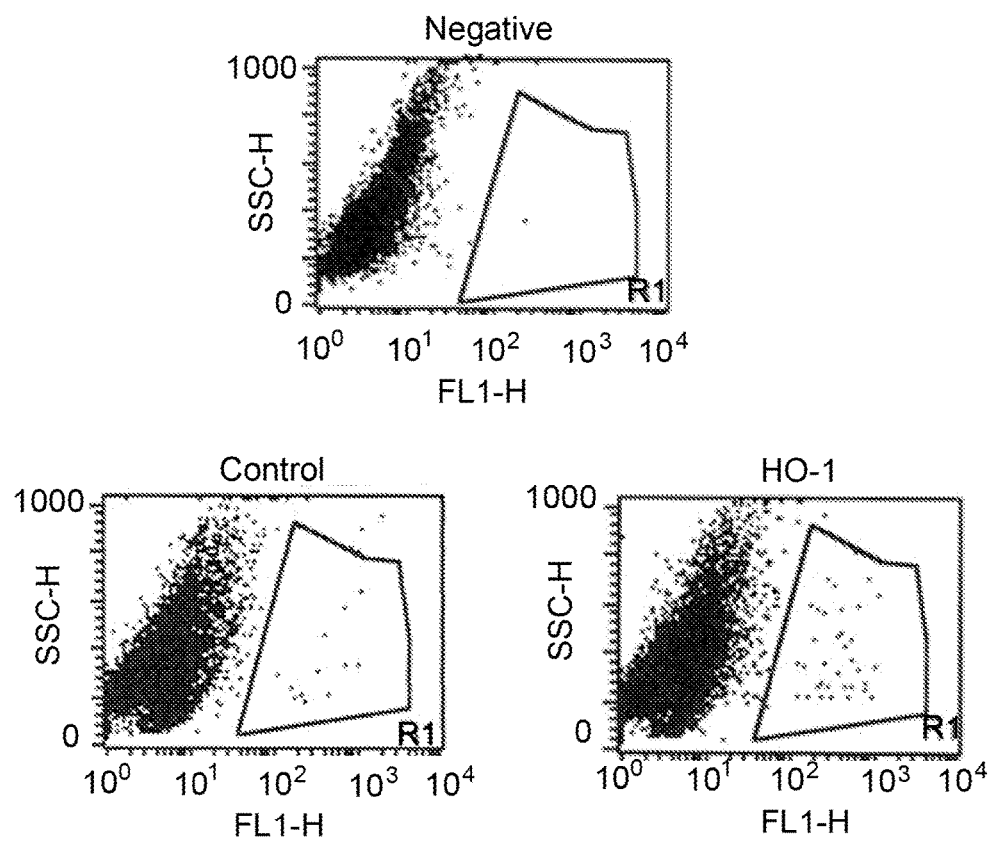
Figure 4E:
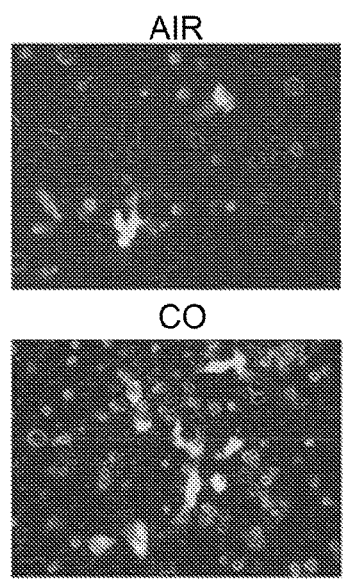
Figure 4F:
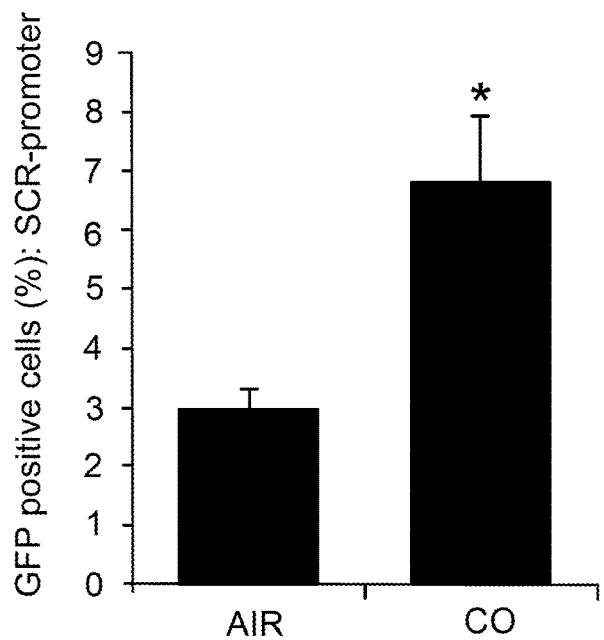

To test the role of HO-1 in DSB, HO-1 was transiently overexpressed together with the I-SceI plasmid in U2OS cells and tested the number of cells positive for GFP 24 hours post-transfection (FIG. 4A). U2OS-SCR reporter cells were co-transfected transiently with SceI and HO-1 or control plasmid. Cells were transfected with HO-1 construct and the amount of GFP-positive cells was measured 48 hours after transfection. A significant 2-fold increase in GFP levels was observed in HO-1 overexpressing cells as assessed by fluorescence microscopy and flow cytometry (FIGS. 4B-D) while control, nontransfected, as well as control-vector-transfected cells showed a low frequency of GFP-positivity indicating poor repair (FIGS. 4F-D). These data support a role for HO-1 in the induction of HR in response to DSB.

Figure 4G:
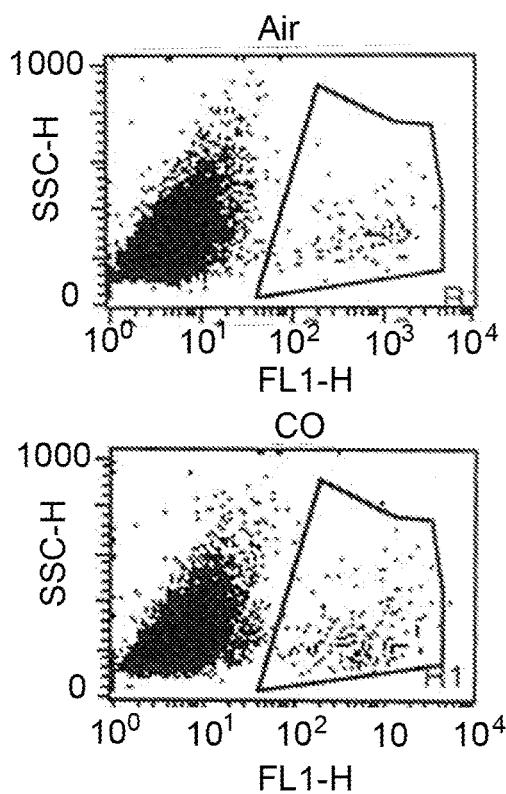

Many of the effects observed with HO-1 are mediated by one or more of its enzymatic products biliverdin or CO. Therefore, the role of biliverdin and CO was tested separately in HR during DSB and DNA repair. U2OS-SCR reporter cells after transfection with SceI for 24 hours were treated with CO 250 (ppm) for 24 hours. Biliverdin treatment had no effect on the number of GFP-positive cells, however CO (250 ppm) significantly increased the number of GFP-positive cells (FIGS. 4E-G) suggesting that HO-1 acts in part via CO to regulate DNA repair pathways and facilitate HR in response to DNA damage. No effects of CO were observed on NHEJ-mediated DNA repair as measured by number of XHATM-resistant colonies.

Figure 5A:
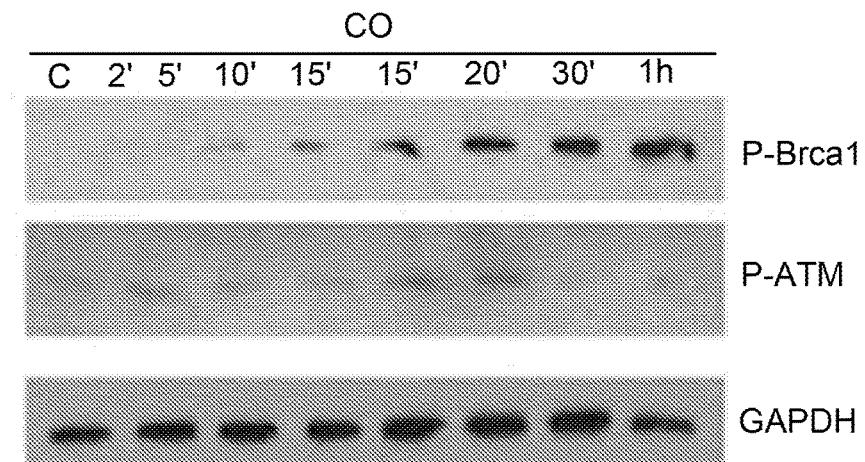
FIGS. 5A-F are a series of figures showing CO induces activation of DNA repair signaling. A-B. Immunoblots with antibody against P-Brca1, P-ATM (A) and P-ATR (B) in the lysates of PC3 and HEK cells that were treated with CO. Data are representative for 3 independent experiments. C-D. Graphs showing the levels of GFP-positive cells were measured by flow cytometry. *p<0.05 CO versus Air; #p<0.05 CO+CGK733 versus CO. E. A bar graph showing the levels of GFP-positive cells were measured by flow cytometry. *p<0.05, CO versus Air, ** p<0.01 CO+KU55933 versus CO; (−) untransfected cells. F. A bar graph showing the level of GFP-positive cells was measured by flow cytometry. Data are representative for 3 independent experiments in duplicates. * p<0.05 HO-1 versus C, # p<0.05 HO-1+CGK733 versus HO-1.
Figure 5B:
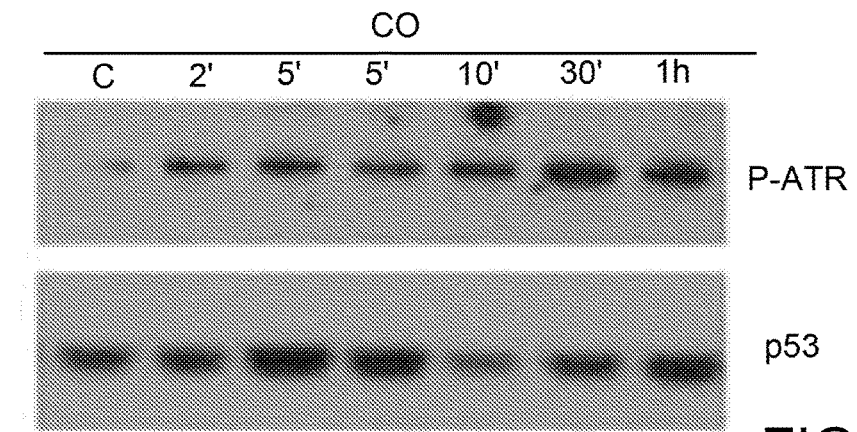
Figure 5C:
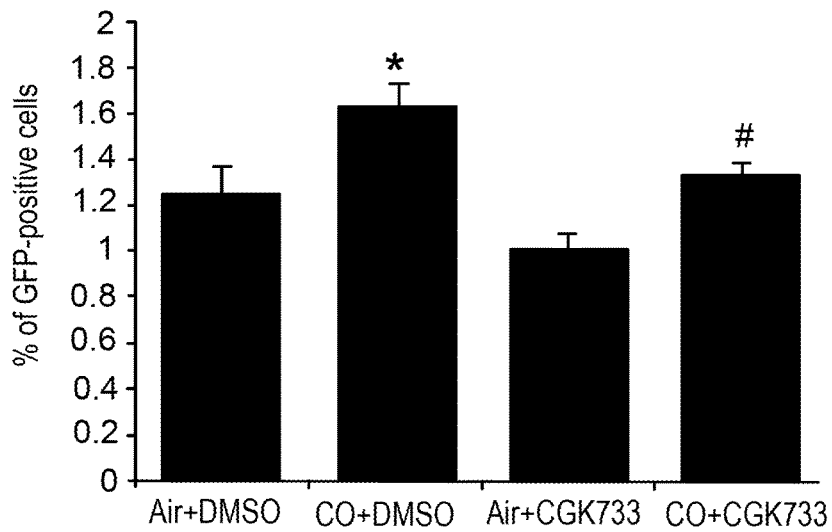
Figure 5D:
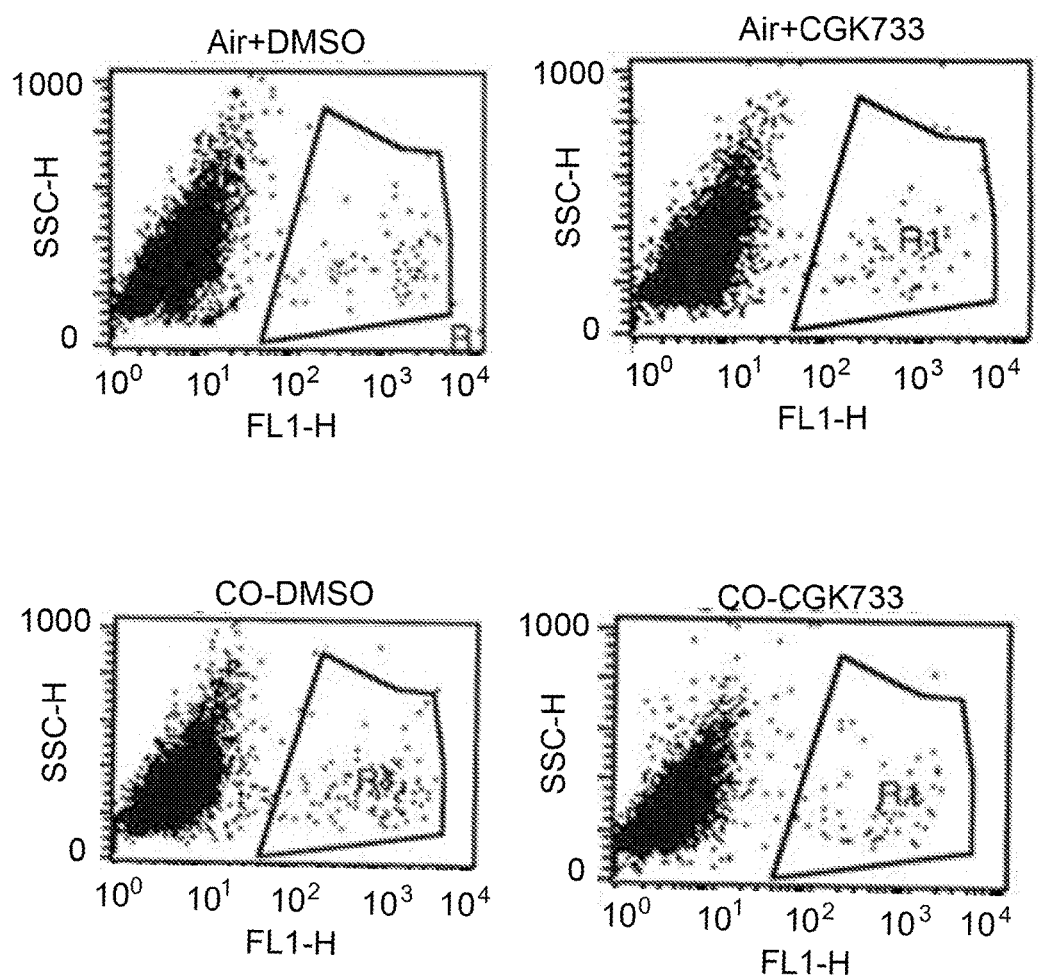
Figure 5E:
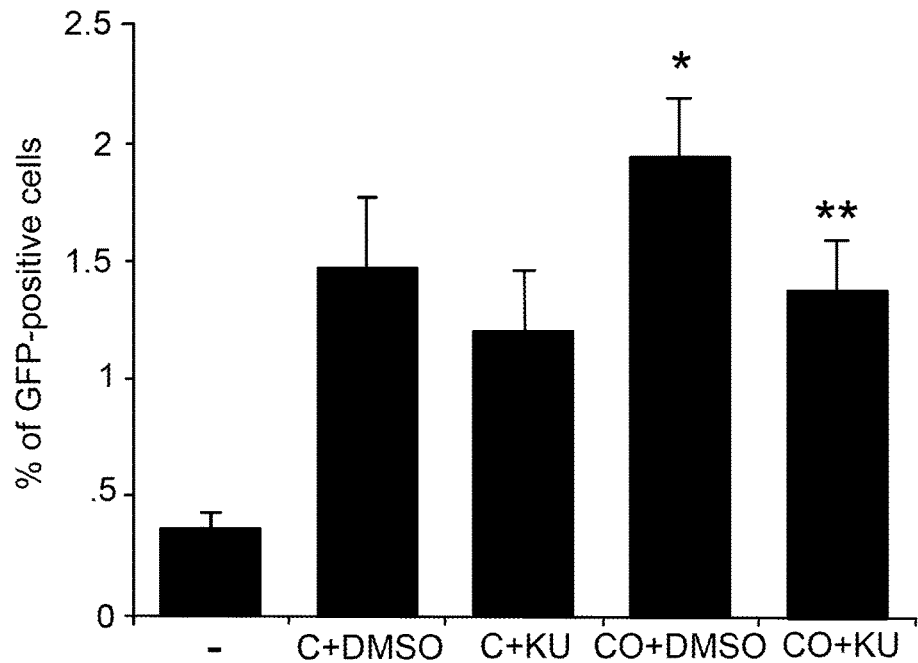
Figure 5F:
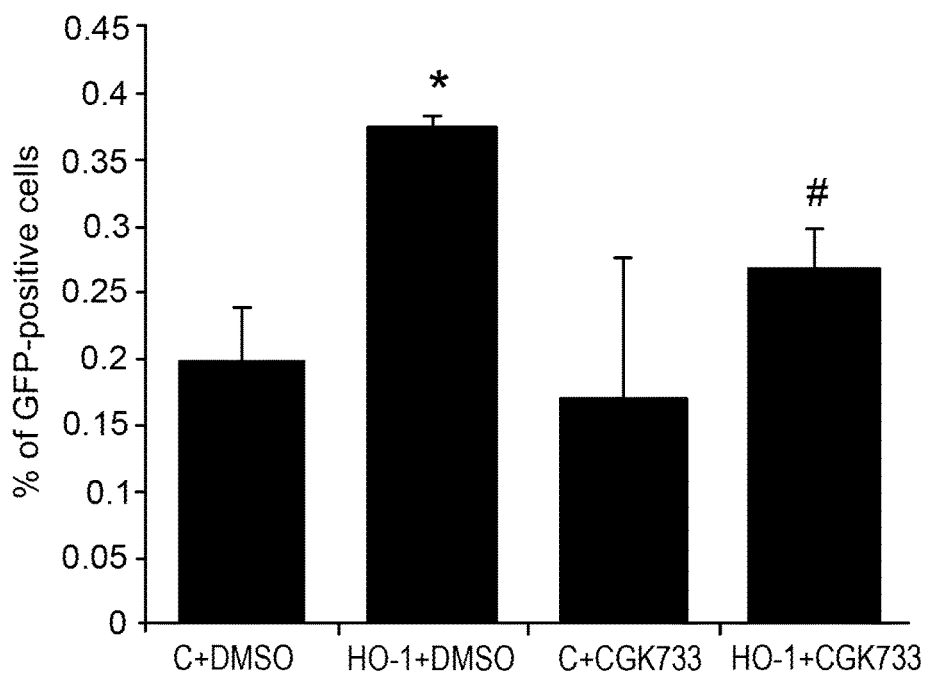
Figure 6F:
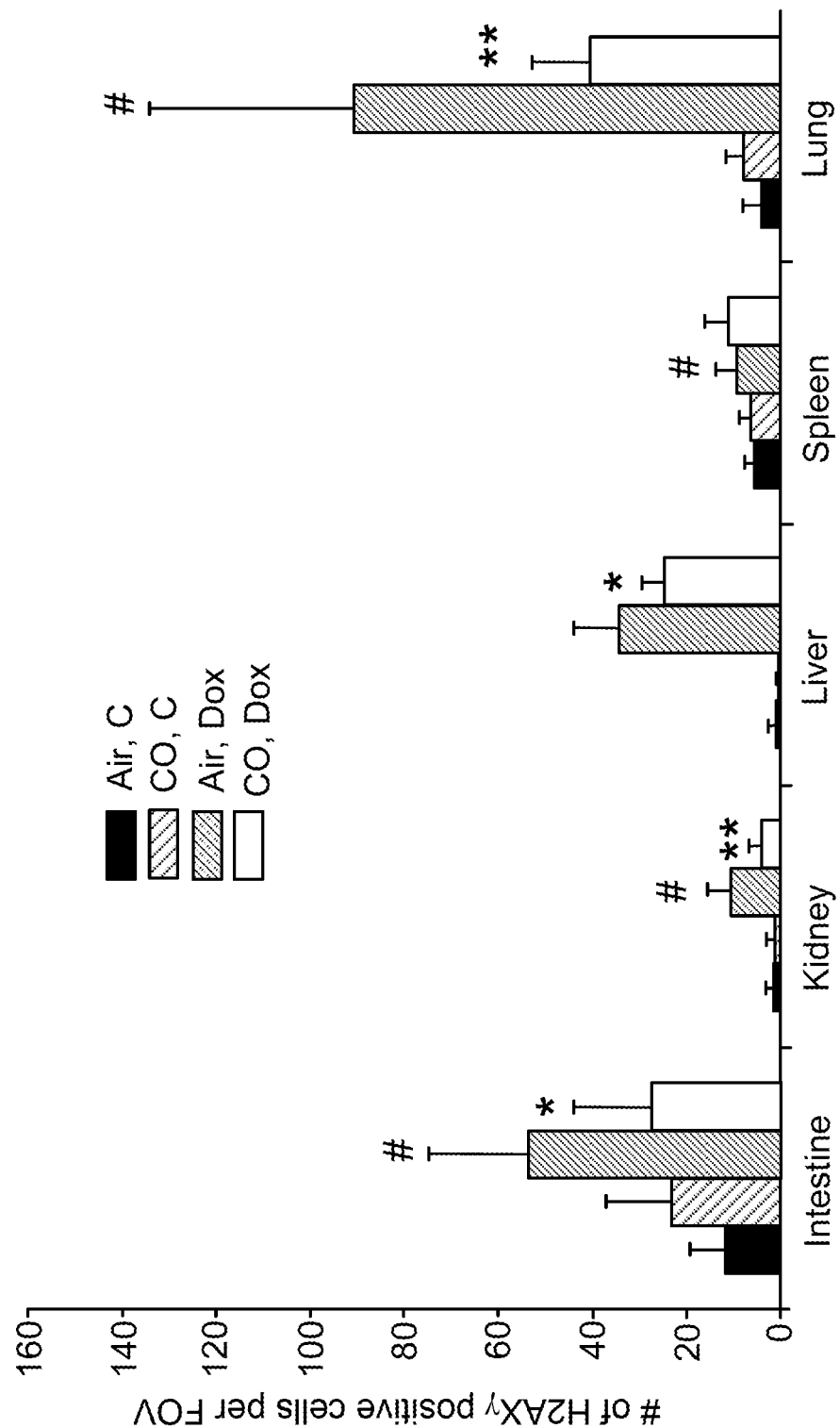

Example 4. DNA Repair Responses Modulated by CO/HO-1 are Dependent on ATM/ATR Activity Lysates of PC3 and HEK cells were treated with CO (250 ppm) for 2' to 1 h. CO induced rapid phosphorylation of Brca1 in HEK cells, as well as the upstream kinases ATR and ATM (FIGS. 5A-5B), suggesting that CO induces DNA repair pathways in cells, which are constantly under risk of oxidative DNA damage. Therefore, the two major DNA repair kinases, ATM and ATR, were examined to see if they are implicated in accelerated HR in the presence of CO or HO-1. The selective inhibitor of ATM and ATR kinases, CGK733, and the more selective inhibitor of ATM, KU55933, was used to test this hypothesis. U20S-SCR reporter cells were transfected with SceI for 24 hours and treated with CGK733 (20 μM) or DMSO for 1 hour prior treatment with CO (250 ppm) for 24 hours. U20S-SCR reporter cells were co-transfected with SceI for 24 hours and KU55933 (20 μM) or DMSO for 1 hour prior treatment with CO (250 ppm) was applied for following 24 hours. Blockade of ATM/ATR or ATM alone significantly decreased CO-mediated HR (FIGS. 5C-E). U20S-SCR reporter cells were co-transfected with SceI and HO-1 for 24 hours and CGK733 was applied for following 24 hours. Induction of HO-1 did not increase HR in the presence of GK733 as otherwise observed in vehicle controls (FIG. 5F) strongly suggesting that both ATR and ATM are utilized by CO/HO-1 in part to regulate HR and DNA repair following damage.

Example 5. CO Protects Against DNA Damage In Vivo in Response to Chemotherapy or Radiation Based on the effects observed in vitro, the salutary effects of CO were tested in an in vivo model of DNA damage in mice. Tissues were harvested 14 days after treatment of nude mice with established PC3 tumors (2 weeks) with CO (Control) or doxorubicin (8 mg/kg, twice per week, i.v.)±CO (daily, 1 hour, 250 ppm). Doxorubicin was employed to induce DNA damage in the tissues during chemotherapeutic treatment of tumor xenografts in nude mice. Doxorubicin led to substantial DNA damage in the lung, liver, kidney and colon and to a lower extent in the spleen as determined by accumulation of H2AXγ foci and was associated with increased expression of HO-1 (FIGS. 6A-E). CO significantly decreased the severity of DNA damage in all organs (FIGS. 6A-F).

Figure 7A:
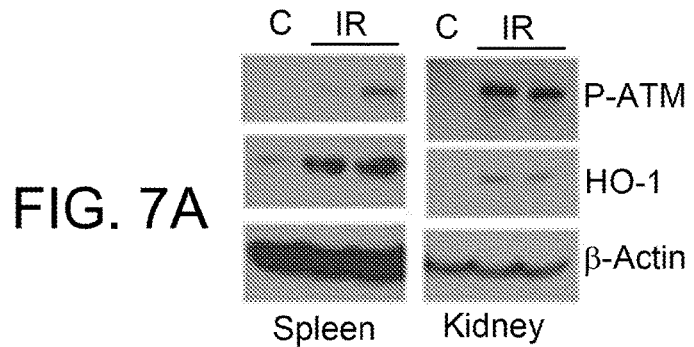
FIGS. 7A-G are a series of photomicrographs and graphs showing CO decreases the lethal dose irradiation induced damage in the tissues. A-B. An immunoblot (A) and immunohistochemistry (B) with antibody against HO-1 in the tissues from mice irradiated with 10 Gy. Liver and spleens after 1 and 3 days post-irradiation are shown in B. C-D. An immunohistochemical analysis of P-H2AX in the spleens and intestines of mice pretreated with Air or CO 1 hour prior lethal dose of irradiation and treated daily with CO for 11 days. Representative pictures are shown in C and quantitation of the number of H2AXg positive cells in D. n=3-4 views/sections; n=3-4 mice/group. E-F. An immunofluorescence staining of P-ATM and P-p53 in mononuclear blood cells of mice that were lethally irradiated and treated with CO/Air for 1 hour prior to irradiation. Representative pictures and quantitation of number of positive cells per field of view is shown. n=3-4/group. G. A graphs showing survival of mice after marginal bone marrow transplantation from H2ax$^{-/-}$ and H2ax$^{+/+}$ mice to the wild type recipients. n=5-10/per group.
Figure 7B:
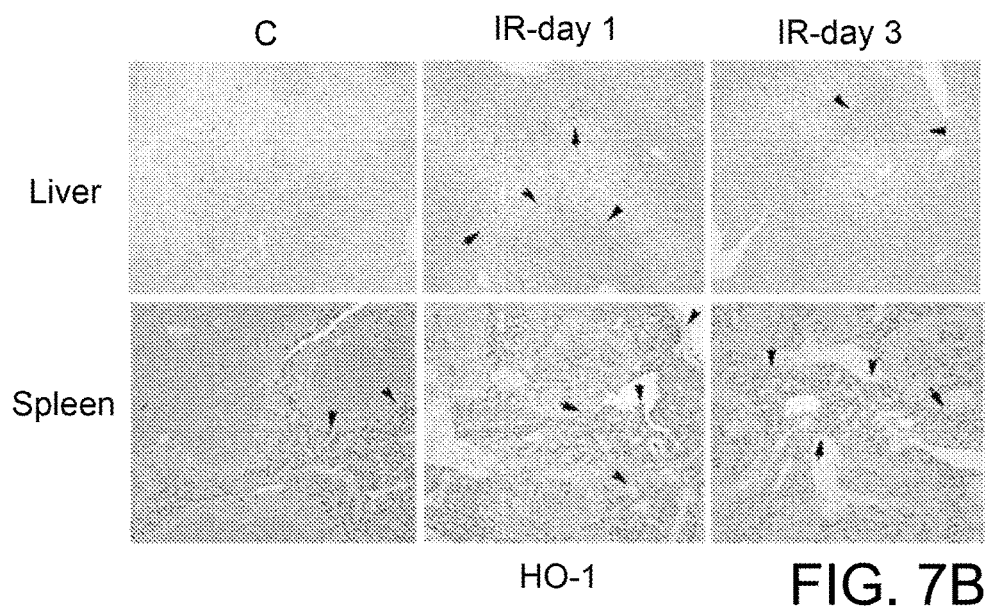
Figure 7C:
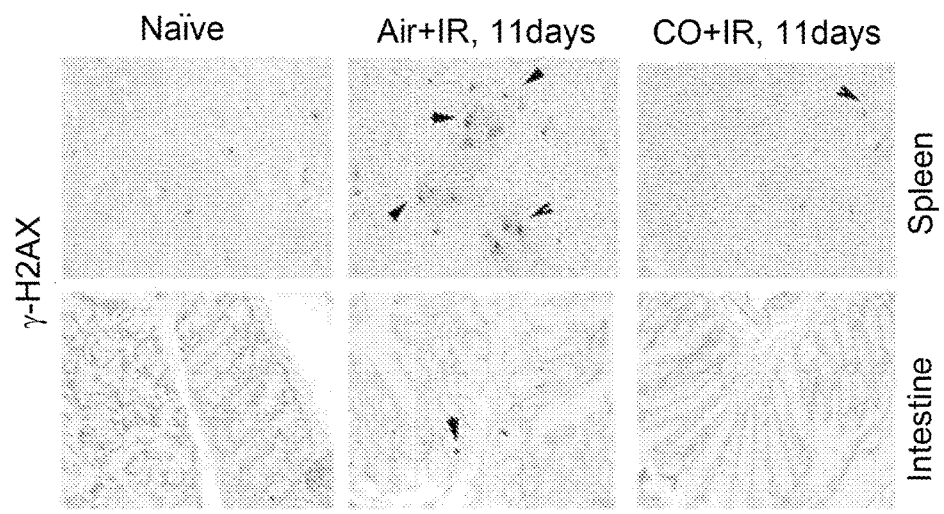
Figure 7D:
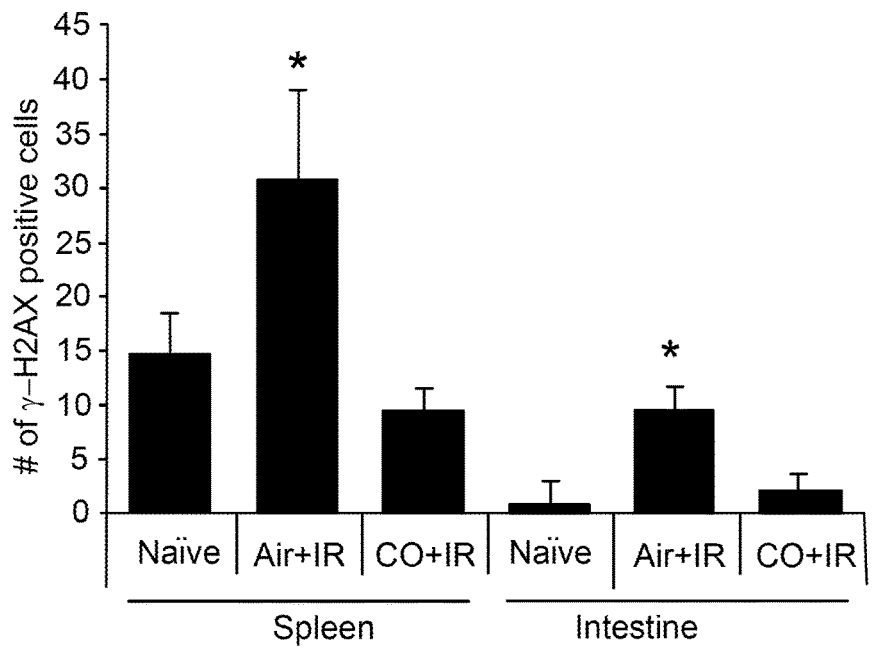
Figure 7E:
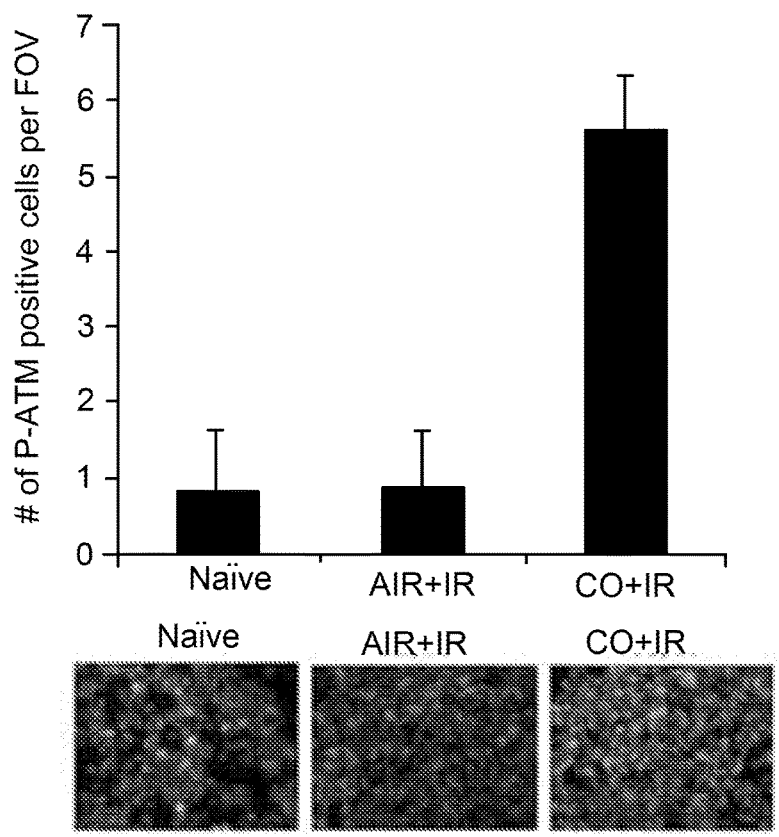
Figure 7F:
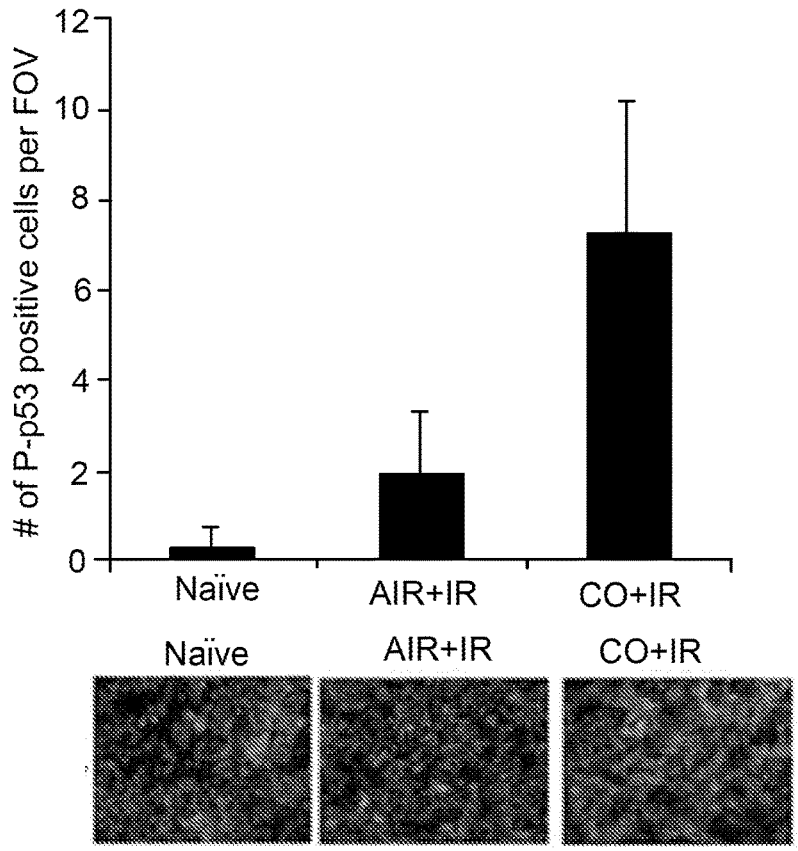
Figure 7G:
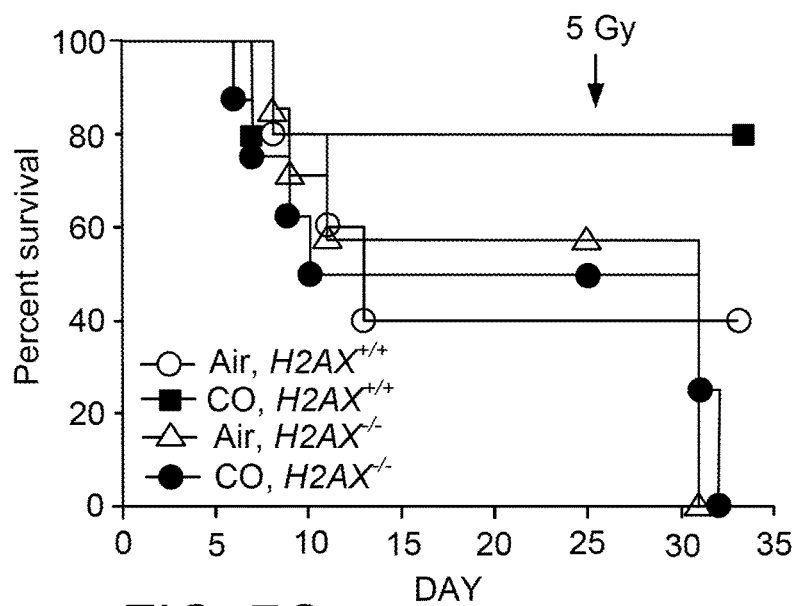

To support the observations with chemical genotoxins, a radiation-induced model of DNA damage was also used. Endogenous HO-1 is induced early in response to IR or doxorubicin and its expression is sustained for 24-72 hours in the spleen, liver and kidney (FIGS. 7A-B). Kidneys and spleen were harvested after 2 hours after irradiation. To evaluate the role of exogenous CO, mice were pretreated with CO for 1 hour prior to either a lethal or sublethal dose of irradiation and then daily for 1 hour. Spleens and intestines of mice were pretreated with Air or CO (250 ppm) 1 hour prior lethal dose of irradiation (10 Gy) and treated daily with CO for 11 days. A chronic elevation of H2AXγ foci was observed in the spleen and intestine of irradiated mice (FIGS. 7C-D). In contrast, treatment of mice with CO led to significant inhibition in sustained H2AXγ foci formation that corresponded to a longer survival rate with 80% of mice alive >10 days vs. 50% in air-treated animals (p=0.031*, CO versus Air, n=6/group). In contrast, there was a strong induction of P-p53, P-Brca1, P-ATM and early induction of P-H2AX in peripheral blood mononuclear cells and bone marrow of irradiated animals treated with CO for 1 hour as compared to air controls suggesting early resolution of DNA damage (FIGS. 7E-F). Tissues were harvested 2 hours after irradiation. To evaluate the role of H2AX signaling in CO effects on DNA repair, marginal bone marrow transplantation of BM cells from H2ax$^{-/-}$ and H2ax$^{+/+}$ mice into wild type irradiated recipients was used. Mice were treated with CO prior lethal dose of irradiation (10 Gy) and thereafter after receiving BM. Lack of H2AX in donor BM cells reversed CO-mediated protection against irradiation-induced death, suggesting a critical role of the H2AX pathway in CO-mediated protection (FIG. 7G).

Example 6. Materials and Methods

Animals, Irradiation and CO Treatment

Male C57BL/6 mice 7-9 weeks of age were purchased from Jackson Laboratories (Bar Harbor, Me.). Mice were held under SPF conditions and the experiments were approved by the IACUC at BIDMC. Mice were irradiated with 10 Gy (lethal dose) or 5 Gy (sublethal dose) and the protocol was approved by Radiation Safety Officer at BIDMC and the IACUC. Mice were exposed in plexiglass chamber to CO for 1 hour, 250 ppm prior irradiation and thereafter every day for 1 hour.

Marginal Bone Marrow Transplant

Mice were lethally irradiated and transplanted with 2.5 min cells i.v. immediately after irradiation. The amount of injected BM was sufficient for recovery of 40% mice.

Nu/nu mice were purchased from Taconic (Hudson, N.Y.) at 7 weeks of age. Those mice were used in a complementary experiment of a subcutaneous tumor model of PC3 cells injected into the right flank of mice. Doxorubicin (8 mg/kg, Sigma) was given i.v. twice per week and mice were exposed to CO daily (250 ppm for 1 hour). Tissues were harvested after 2 weeks of treatment.

Cell Culture and Treatment

U203 HR/SCR cells were maintained in the DMEM medium (Gibco, Invitrogen) containing 10% FBS and antibiotics. pPHW1 cells (NHEJ model) were maintained in the DMEM medium with 10% FBS and antibiotics. Mouse kidney fibroblasts were obtained from adult Hmox1$^{-/-}$ and Hmox1$^{+/+}$ mice and culture between passages 4-7 in DMEM medium supplemented with 10% FBS and antibiotics. HEK293 were purchased from ATCC and were cultured following manufacturer's protocol. For CO in vitro studies, cells were exposed to 250 ppm CO, 5% $CO_2$ in 95% $N_2$ for 2 minutes to 24 hours. Cells were irradiated with 10 Gy and harvested at different time points after single exposure.

ShmirRNA Retroviral Mediated Transfections

MicroRNA-adapted shRNA (shRNAmir) for human HO-1 was purchased from Open Biosystems (AL, USA). shRNAmir-HO-1 was subcloned to MSCV-LTRmiR30-PIG (LMP) vector (Open Biosystems) with XhoI and EcoRI restriction enzymes. The retrovirus for LMP-shRNAHO-1 and control vector were produced and used for transduction of HEK-293 cells. Stable clones were generated by selection with 5 μg/ml puromycin (Sigma) for 2-4 weeks.

HR/SCR Reporter Assay, Flow Cytometry and Fluorescence Microscopy

HR/SCR reporter U20S cells were used as previously described. Briefly, GFP+ cells were analyzed 2 days postransfection by flow cytometry (FACScan, BD Biosciences) and fluorescence microscopy. Images of GFP-positive cells were captured of randomized fields using a Zeiss Apotome fluorescent microscope.

Statistical Analyses

The significance of differences was determined using analysis of variance (ANOVA) or Student t-test (SPSS Inc, Chicago, Ill.) with significance accepted at p<0.05. For survival analysis Log Rank Mantel Cox test was applied.

Example 7. Carbon Monoxide in Aging and Senescence

This example demonstrates that heme oxygenase-1 and CORM inhibit the senescence-associated β-galactosidase staining in a zebrafish embryo model of aging.

Figure 8:
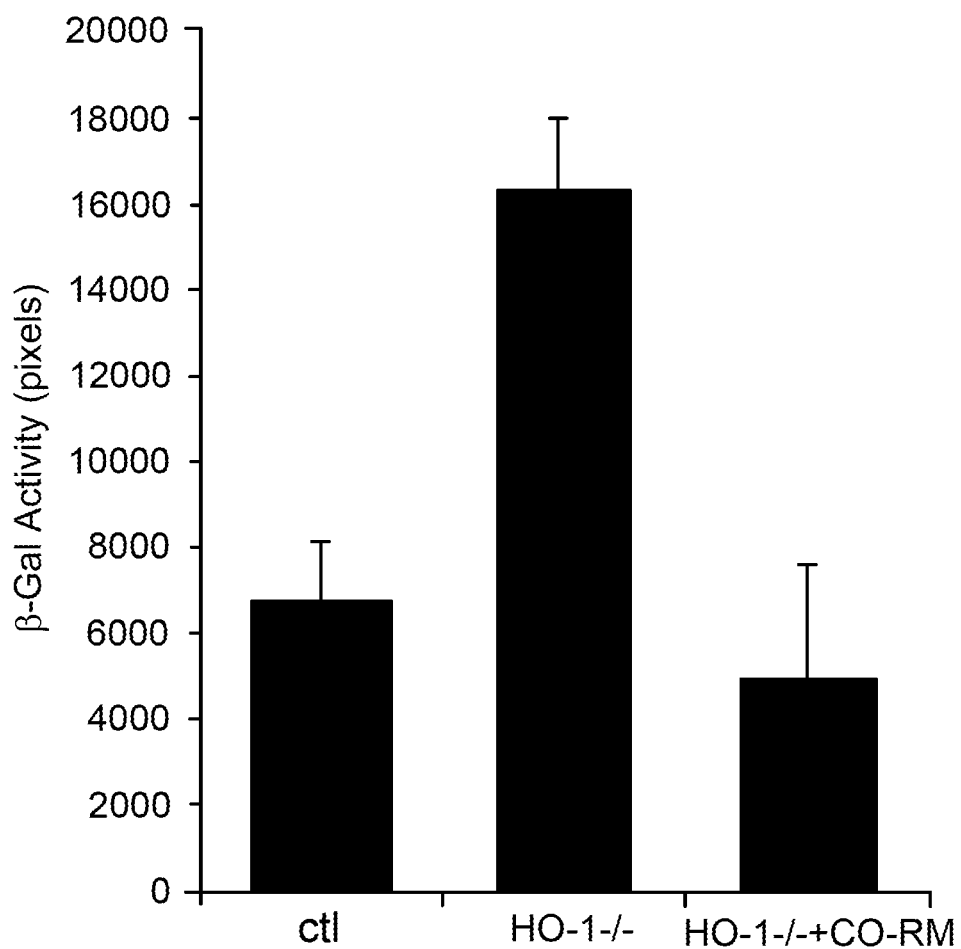
FIG. 8 is a bar graph depicting beta-galactosidase activity in zebra fish embryos as an accepted measure of senesence.

A model of senescence in vivo in the zebrafish embryos was employed as previously described (Koshimizu et al., 2011, Plos One, 6:e17688). Embryos were either transfected with a morpholino to inhibit HO-1 expression or a control vector. In a separate treatment group, embryos were transfected with the HO-1 morpholino and treated with a CO-releasing molecule (50 µM; Sigma-Aldrich). Results show that embryos lacking HO-1 have a greater β-gal activity indicating greater or more rapid senescence and that CO administration can reverse this to a normal senescence/aging level of positive β-gal staining, trending towards slowing of senescence. Knockdown of HO-1 with morpholinos against HO-1 in zebrafish embryos resulted in induction of senescence-associated β-galactosidase (SA-β-gal) activity as compared to control morpholinos or non-injected larvae (FIG. 8). A slowing of senescence of zebrafish embryos was observed with application of CORM after injection with morpholinos against HO-1 (FIG. 8). These data suggest that aging associated senescence that is accelerated in the absence of HO-1 can be reversed by application of CO.

Figure 9A:
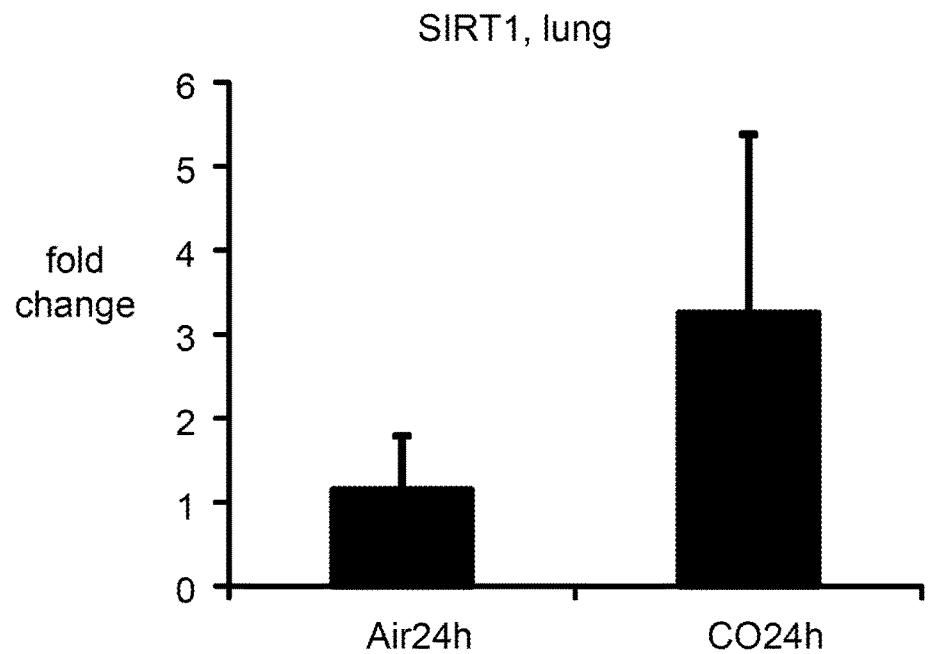
FIGS. 9A-B are a series of two bar graphs showing CO exposure increases gene expression of SIRT1 (9A) and TERT (9B) in vivo.
Figure 9B:
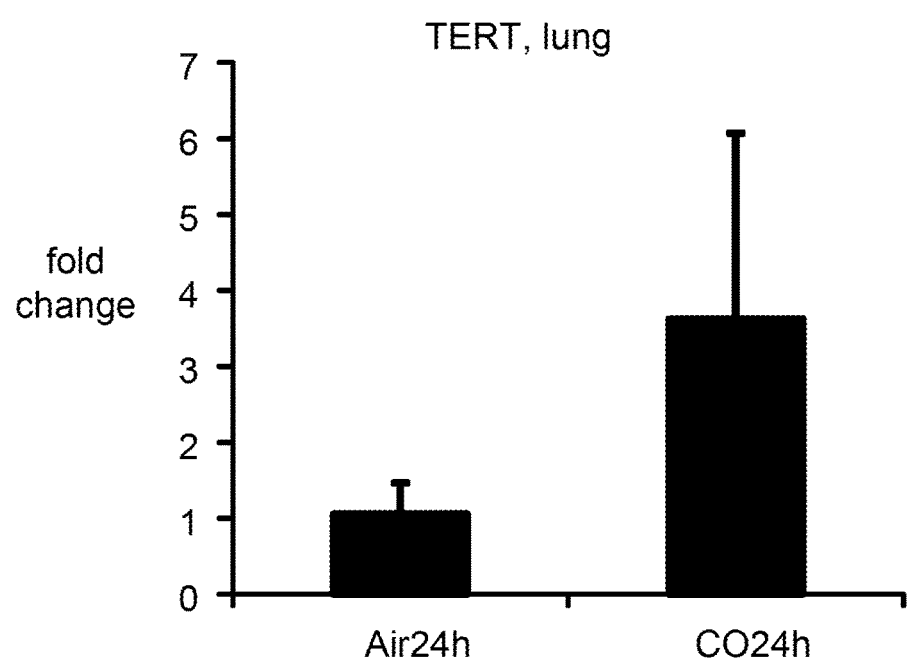

In another set of experiments performed in mice, mice were exposed to CO for 1 hour and harvested multiple tissues at 24 hours and found that animals treated with CO had increased expression of the anti-aging genes SIRT1 (sirtuin; FIG. 9A) and TERT (telomerase reverse transcriptase; FIG. 9B) in the lung. This is important given that the lung has such a high rate of cellular turnover. The increase in expression of these genes is associated with decreased senescence and extension of life span.

Example 8. CO in DNA Repair

This example demonstrates that exposure to CO increases expression of telomerase, topoisomerase, and p16 to decrease DNA damage.

Figure 10:
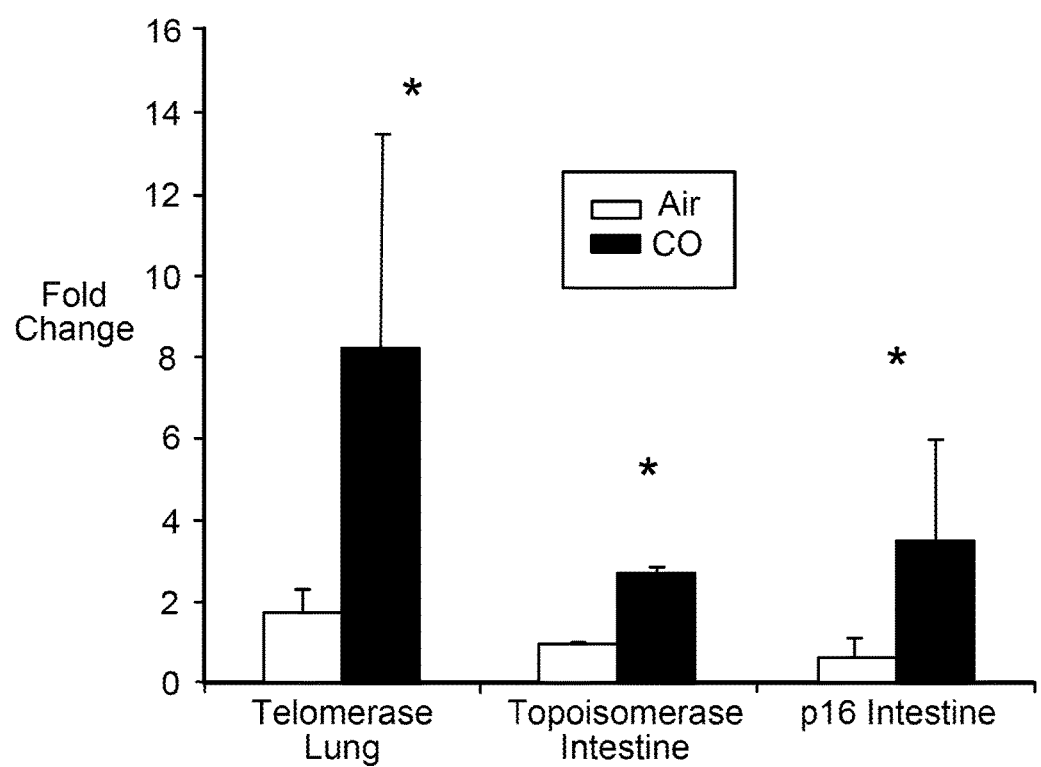
FIG. 10 is a bar graph showing change in expression of telomerase in lung, and topoisomerase and p16 in intestine. Results represent mean±SD of at least 3 mice/group, * p<0.05.

Male C57Bl/6 mice were exposed to inhaled carbon monoxide at 250 parts per million (ppm) for 1 hour. Mice were immediately removed from the exposure chamber and the lungs and intestines were harvested and processed for RNA. Real time PCR for telomerase in lungs, and topoisomerase (responsible for unwinding of DNA) and p16 (cell cycle suppressor) in intestines was performed, and expression was compared to air-exposed controls (FIG. 10). Results represent mean±SD of at least 3 mice/group, * p<0.05.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of reducing radiation-induced DNA damage in a subject, the method comprising:
administering to a subject whose substantially whole body has been exposed to an acute dose of a DNA-damaging level of ionizing radiation, and who exhibits symptoms of radiation-induced DNA damage, a pharmaceutical composition comprising an amount of carbon monoxide effective to reduce radiation-induced DNA damage in the subject, the pharmaceutical composition being administered intermittently or continuously until the subject no longer exhibits symptoms of DNA damage.

2. The method of claim 1, wherein the ionizing radiation is from a nuclear reactor or nuclear weapon.

3. The method of claim 1, wherein the pharmaceutical composition is in gaseous form and is administered to the subject by inhalation.

4. The method of claim 1, wherein the pharmaceutical composition is in liquid form and is administered to the subject orally.

5. The method of claim 1, wherein the acute dose of ionizing radiation is at least one Gray.

6. The method of claim 1, wherein the pharmaceutical composition is administered directly to the abdominal cavity of the subject.

7. The method of claim 1, wherein the pharmaceutical composition comprises a carbon monoxide-releasing compound.

8. The method of claim 1, wherein the pharmaceutical composition is administered by an artificial lung.

9. The method of claim 1, wherein the pharmaceutical composition is administered by an extracorporeal membrane gas exchange device.

10. The method of claim 1, wherein the pharmaceutical composition is administered for about 1, 2, 3, 5, or 6 months.

11. The method of claim 1, wherein the pharmaceutical composition is administered to the subject immediately after the subject being exposed to ionizing radiation.

12. The method of claim 1, wherein the pharmaceutical composition is administered to the subject by acute administration.

13. The method of claim 1, wherein the method induces DNA repair process.

14. A method of reducing DNA damage in a subject during warfare or an act of terrorism, the method comprising:
administering to a subject who has been exposed to DNA-damaging levels of radiation from an explosion of a nuclear weapon and who exhibits symptoms of radiation-induced DNA damage, a pharmaceutical composition comprising an amount of carbon monoxide effective to reduce DNA damage in the subject, the pharmaceutical composition being administered intermittently or continuously until the subject no longer exhibits symptoms of DNA damage.

15. The method of claim 14, wherein the pharmaceutical composition is in gaseous form and is administered to the subject by inhalation.

16. The method of claim 14, wherein the pharmaceutical composition is in liquid form and is administered to the subject orally.

17. The method of claim 14, wherein the pharmaceutical composition is administered directly to the abdominal cavity of the subject.

18. The method of claim 14, wherein the pharmaceutical composition comprises a carbon monoxide-releasing compound.

19. The method of claim 14, wherein the pharmaceutical composition is administered by an artificial lung.

20. The method of claim 14, wherein the pharmaceutical composition is administered by an extracorporeal membrane gas exchange device.

21. The method of claim 14, wherein the pharmaceutical composition is administered for about 1, 2, 3, 5, or 6 months.

22. The method of claim 14, wherein the pharmaceutical composition is administered to the subject immediately after the subject being exposed to radiation.

23. The method of claim 14, wherein the pharmaceutical composition is administered to the subject by acute administration.

24. The method of claim 14, wherein the method induces DNA repair process.

25. A method of reducing hyperthermia-induced DNA damage in a subject, the method comprising:
   identifying a subject whose whole body has been exposed to DNA-damaging levels of hyperthermia, and who exhibits symptoms of hyperthermia-induced DNA damage; and
   administering to the subject a pharmaceutical composition comprising an amount of carbon monoxide effective to reduce hyperthermia-induced DNA damage in the subject, the pharmaceutical composition being administered intermittently or continuously until the subject no longer exhibits symptoms of DNA damage.

26. The method of claim 25, wherein the pharmaceutical composition is in gaseous form and is administered to the subject by inhalation.

27. The method of claim 25, wherein the pharmaceutical composition is in liquid form and is administered to the subject orally.

28. The method of claim 25, wherein the pharmaceutical composition is administered directly to the abdominal cavity of the subject.

29. The method of claim 25, wherein the pharmaceutical composition comprises a carbon monoxide-releasing compound.

30. The method of claim 25, wherein the pharmaceutical composition is administered by an artificial lung.

31. The method of claim 25, wherein the pharmaceutical composition is administered by an extracorporeal membrane gas exchange device.

32. The method of claim 25, wherein the pharmaceutical composition is administered for about 1, 2, 3, 5, or 6 months.

33. A method of treating acute radiation syndrome in a subject, the method comprising:
   administering to a subject whose substantially whole body has been exposed to an acute dose of a DNA-damaging level of ionizing radiation, and who is diagnosed as having acute radiation syndrome, a pharmaceutical composition comprising an amount of carbon monoxide effective to reduce radiation-induced DNA damage in the subject, the pharmaceutical composition being administered intermittently or continuously until the subject no longer exhibits symptoms of DNA damage.

34. The method of claim 33, wherein the ionizing radiation is from a nuclear reactor or nuclear weapon.

35. The method of claim 33, wherein the acute dose of ionizing radiation is at least one Gray.

36. The method of claim 33, wherein the pharmaceutical composition is in gaseous form and is administered to the subject by inhalation.

37. The method of claim 33, wherein the pharmaceutical composition is in liquid form and is administered to the subject orally.

38. The method of claim 33, wherein the pharmaceutical composition is administered directly to the abdominal cavity of the patient.

39. The method of claim 33, wherein the pharmaceutical composition comprises a carbon monoxide-releasing compound.

40. The method of claim 33, wherein the pharmaceutical composition is administered by an artificial lung.

41. The method of claim 33, wherein the pharmaceutical composition is administered by an extracorporeal membrane gas exchange device.

42. The method of claim 33, wherein the pharmaceutical composition is administered for about 1, 2, 3, 5, or 6 months.

43. The method of claim 33, wherein the pharmaceutical composition is administered to the subject immediately after the subject being exposed to ionizing radiation.

44. The method of claim 33, wherein the pharmaceutical composition is administered to the subject by acute administration.

45. The method of claim 33, wherein the method induces DNA repair process.

* * * * *